United States Patent [19]
Lipshutz et al.

[11] Patent Number: 6,066,454
[45] Date of Patent: *May 23, 2000

[54] COMPUTER-AIDED PROBABILITY BASE CALLING FOR ARRAYS OF NUCLEIC ACID PROBES ON CHIPS

[75] Inventors: Robert J. Lipshutz, Palo Alto; Michael G. Walker, Sunnyvale, both of Calif.

[73] Assignee: Affymetrix, Inc., Santa Clara, Calif.

[*] Notice: This patent is subject to a terminal disclaimer.

[21] Appl. No.: 08/948,896

[22] Filed: Oct. 10, 1997

Related U.S. Application Data

[63] Continuation of application No. 08/528,656, Sep. 14, 1995, Pat. No. 5,733,729.

[51] Int. Cl.$^7$ .............................. C12Q 1/68; C07H 21/04; G06K 9/18
[52] U.S. Cl. .............................. 435/6; 436/497; 536/23.1; 536/24.32; 382/129
[58] Field of Search ....................... 435/6, 973; 536/23.1, 536/24.3, 24.31, 24.32; 935/78; 436/497; 382/129

[56] References Cited

U.S. PATENT DOCUMENTS

| | | | |
|---|---|---|---|
| 5,002,867 | 3/1991 | Macevicz | 435/6 |
| 5,143,854 | 9/1992 | Pirrung et al. | 436/518 |
| 5,202,231 | 4/1993 | Drmanac et al. | 435/6 |
| 5,235,626 | 8/1993 | Flamholz et al. | 378/34 |
| 5,288,514 | 2/1994 | Ellman | 427/2 |
| 5,365,455 | 11/1994 | Tibbetts et al. | 364/497 |
| 5,384,261 | 1/1995 | Winkler et al. | 436/518 |
| 5,445,934 | 8/1995 | Fodor et al. | 435/6 |
| 5,470,710 | 11/1995 | Weiss et al. | 435/6 |
| 5,502,773 | 3/1996 | Tibbetts et al. | 382/129 |
| 5,503,980 | 4/1996 | Cantor | 435/6 |

FOREIGN PATENT DOCUMENTS

| | | |
|---|---|---|
| WO 89/10977 | 11/1989 | WIPO . |
| WO 92/10092 | 6/1992 | WIPO . |
| WO 92/10588 | 6/1992 | WIPO . |
| WO 95/11995 | 5/1995 | WIPO . |

OTHER PUBLICATIONS

Fodor et al., "Light–Directed Spatially Addressable Parallel Chemical Synthesis," Science, vol. 251, Feb. 15, 1991, pp. 767–773.

Brown et al., An Inexpensive MSI/LSI Mask Making System, Proceedings of 1981 Univ. Govt. Indus. Microelec. Symposium, May 26–27, 1981, pp. III–31 through III–38.

Dear et al., "A Sequence Assembly And Editing Program For Efficient Management of Large Projects," Nucleic Acids Research, vol. 19, No. 14, 1991 Oxford Univ. Press, pp. 3907–3911.

R. Drmanac et al., "Journal of Biomolecular Structure & Dynamics," 8(5): 1085–1102, 1991.

*Primary Examiner*—Stephanie Zitomer
*Assistant Examiner*—Betty J Forman
*Attorney, Agent, or Firm*—Ritter, Van Pelt & Yi

[57] ABSTRACT

A computer system for analyzing nucleic acid sequences is provided. The computer system is used to calculate probabilities for determining unknown bases by analyzing the fluorescence intensities of hybridized nucleic acid probes on biological chips. Additionally, information from multiple experiments is utilized to improve the accuracy of calling unknown bases.

38 Claims, 8 Drawing Sheets

COMPUTER-AIDED PROBABILITY BASE CALLING FOR ARRAYS OF NUCLEIC ACID PROBES ON CHIPS

This is a continuation application of prior application Ser. No. 08/528,656 filed on Sep. 14, 1995, now U.S. Pat. No. 5,733,729, the disclosure of which is incorporated herein by reference.

GOVERNMENT RIGHTS NOTICE

Portions of the material in this specification arose under the cooperative agreement 70NANB5H1031 between Affymetrix, Inc. and the Department of Commerce through the National Institute of Standards and Technology.

COPYRIGHT NOTICE

A portion of the disclosure of this patent document contains material which is subject to copyright protection. The copyright owner has no objection to the xerographic reproduction by anyone of the patent document or the patent disclosure in exactly the form it appears in the Patent and Trademark Office patent file or records, but otherwise reserves all copyright rights whatsoever.

SOFTWARE APPENDIX

A Software Appendix comprising twenty one (21) sheets is included herewith.

BACKGROUND OF THE INVENTION

The present invention relates to the field of computer systems. More specifically, the present invention relates to computer systems for evaluating and comparing biological sequences.

Devices and computer systems for forming and using arrays of materials on a substrate are known. For example, PCT application WO92/10588, incorporated herein by reference for all purposes, describes techniques for sequencing or sequence checking nucleic acids and other materials. Arrays for performing these operations may be formed in arrays according to the methods of, for example, the pioneering techniques disclosed in U.S. Pat. No. 5,143,854 and U.S. patent application Ser. No. 08/249,188, now U.S. Pat. No. 5,571,639, both incorporated herein by reference for all purposes.

According to one aspect of the techniques described therein, an array of nucleic acid probes is fabricated at known locations on a chip or substrate. A fluorescently labeled nucleic acid is then brought into contact with the chip and a scanner generates an image file (also called a cell file) indicating the locations where the labeled nucleic acids bound to the chip. Based upon the image file and identities of the probes at specific locations, it becomes possible to extract information such as the monomer sequence of DNA or RNA. Such systems have been used to form, for example, arrays of DNA that may be used to study and detect mutations relevant to cystic fibrosis, the P53 gene (relevant to certain cancers), HIV, and other genetic characteristics.

Innovative computer-aided techniques for base calling are disclosed in U.S. patent application Ser. No. 08/327,525, which is incorporated by reference for all purposes. However, improved computer systems and methods are still needed to evaluate, analyze, and process the vast amount of information now used and made available by these pioneering technologies.

SUMMARY OF THE INVENTION

An improved computer-aided system for calling unknown bases in sample nucleic acid sequences from multiple nucleic acid probe intensities is disclosed. The present invention is able to call bases with extremely high accuracy (up to 98.5%). At the same time, confidence information may be provided that indicates the likelihood that the base has been called correctly. The methods of the present invention are robust and uniformly optimal regardless of the experimental conditions.

According to one aspect of the invention, a computer system is used to identify an unknown base in a sample nucleic acid sequence by the steps of: inputting a plurality of hybridization probe intensities, each of the probe intensities corresponding to a nucleic acid probe; for each of the plurality of probe intensities, determining a probability that the corresponding nucleic acid probe best hybridizes with the sample nucleic acid sequence; and calling the unknown base according to the nucleic acid probe with the highest associated probability.

According to another aspect of the invention, an unknown base in a sample nucleic acid sequence is called by a base call with the highest probability of correctly calling the unknown base. The unknown base in the sample nucleic acid sequence is identified by the steps of: inputting multiple base calls for the unknown base, each of the base calls having an associated probability which represents a confidence that the unknown base is called correctly; selecting a base call that has a highest associated probability; and calling the unknown base according to the selected base call. The multiple base calls are typically produced from multiple experiments. The multiple experiments may be performed on the same chip utilizing different parameters (e.g., nucleic acid probe length).

According to yet another aspect of the invention, an unknown base in a sample nucleic acid sequence is called according to multiple base calls that collectively have the highest probability of correctly calling the unknown base. The unknown base in the sample nucleic acid sequence is identified by the steps of: inputting multiple probabilities for each possible base for the unknown base, each of the probabilities representing a probability that the unknown base is an associated base; producing a product of probabilities for each possible base, each product being associated with a possible base; and calling the unknown base according to a base associated with a highest product. The multiple base calls are typically produced from multiple experiments. The multiple experiments may be performed on the same chip utilizing different parameters (e.g., nucleic acid probe length).

According to another aspect of the invention, both strands of a DNA molecule are analyzed to increase the accuracy of identifying an unknown base in a sample nucleic acid sequence by the steps of: inputting a first base call for the unknown base, the first base call determined from a first nucleic acid probe that is equivalent to a portion of the sample nucleic acid sequence including the unknown base; inputting a second base call for the unknown base, the second base call determined from a second nucleic acid probe that is complementary to a portion of the sample nucleic acid sequence including the unknown base; selecting one of the first or second nucleic acid probes that has a base at an interrogation position which has a high probability of producing correct base calls; and calling the unknown base according to the selected one of the first or second nucleic acid probes.

A further understanding of the nature and advantages of the inventions herein may be realized by reference to the remaining portions of the specification and the attached drawings.

DESCRIPTION OF THE PREFERRED EMBODIMENT

Contents

I. General
II. Probability Base Calling Method
III. Maximum Probability Method
IV. Product of Probabilities Method
V. Wild-Type Base Preference Method
VI. Software Appendix

I. General

In the description that follows, the present invention will be described in reference to a Sun Workstation in a UNIX environment. The present invention, however, is not limited to any particular hardware or operating system environment. Instead, those skilled in the art will find that the systems and methods of the present invention may be advantageously applied to a variety of systems, including IBM personal computers running MS-DOS or Microsoft Windows. Therefore, the following description of specific systems are for purposes of illustration and not limitation.

Figure 1:
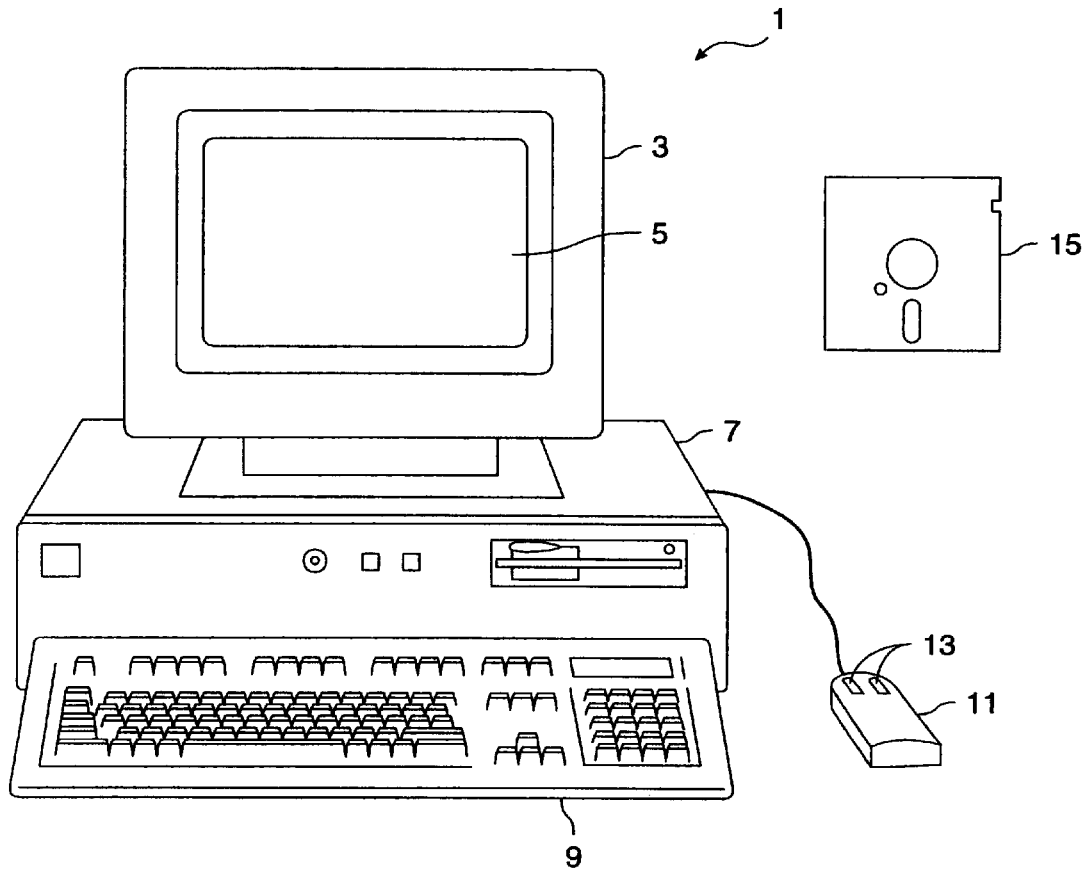
FIG. 1 illustrates an example of a computer system used to execute the software of the present invention.

FIG. 1 illustrates an example of a computer system used to execute the software of the present invention. FIG. 1 shows a computer system 1 which includes a monitor 3, screen 5, cabinet 7, keyboard 9, and mouse 11. Mouse 11 may have one or more buttons such as mouse buttons 13. Cabinet 7 houses a floppy disk drive 14 and a hard drive (not shown) that may be utilized to store and retrieve software programs incorporating the present invention. Although a floppy disk 15 is shown as the removable media, other removable tangible media including CD-ROM and tape may be utilized. Cabinet 7 also houses familiar computer components (not shown) such as a processor, memory, and the like.

Figure 2:
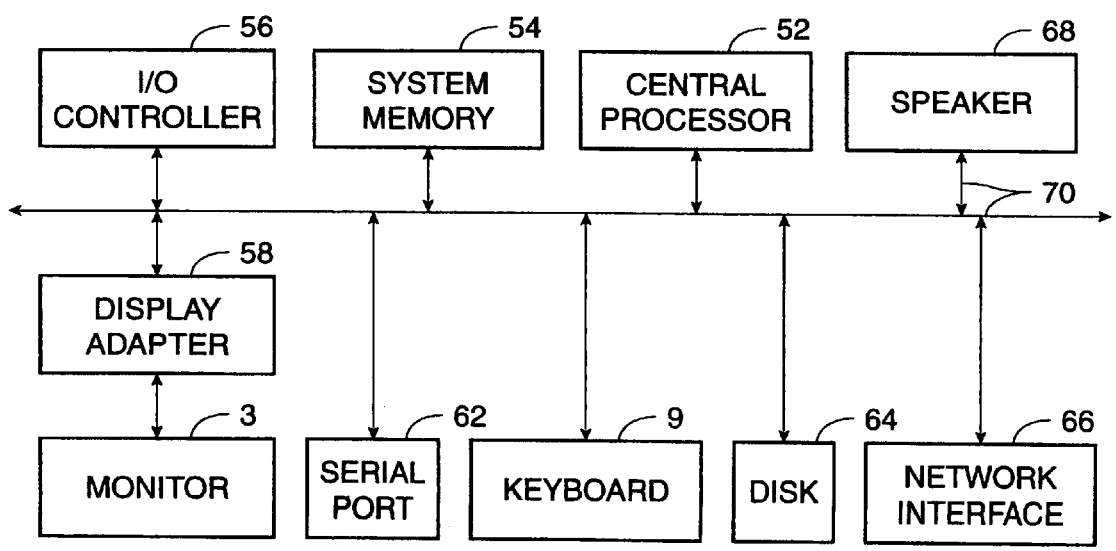
FIG. 2 shows a system block diagram of a typical computer system used to execute the software of the present invention.

FIG. 2 shows a system block diagram of computer system 1 used to execute the software of the present invention. As in FIG. 1, computer system 1 includes monitor 3 and keyboard 9. Computer system 1 further includes subsystems such as a central processor 52, system memory 54, I/O controller 56, display adapter 58, serial port 62, disk 64, network interface 66, and speaker 68. Other computer systems suitable for use with the present invention may include additional or fewer subsystems. For example, another computer system could include more than one processor 52 (i.e., a multi-processor system) or memory cache.

Arrows such as 70 represent the system bus architecture of computer system 1. However, these arrows are illustrative of any interconnection scheme serving to link the subsystems. For example, speaker 68 could be connected to the other subsystems through a port or have an internal direct connection to central processor 52. Computer system 1 shown in FIG. 2 is but an example of a computer system suitable for user with the present invention. Other configurations of subsystems suitable for use with the present invention will be readily apparent to one of ordinary skill in the art.

The VLSIPS technology provides methods of making very large arrays of oligonucleotide probes on very small chips. See U.S. Pat. No. 5,143,854 and PCT patent publication Nos. WO 90/15070 and 92/10092, each of which is incorporated by reference for all purposes. The oligonucleotide probes on the "DNA chip" are used to detect complementary nucleic acid sequences in a sample nucleic acid of interest (the "target" nucleic acid).

The present invention provides methods of analyzing hybridization intensity files for a chip containing hybridized nucleic acid probes. In a representative embodiment, the files represent fluorescence data from a biological array, but the files may also represent other data such as radioactive intensity data. Therefore, the present invention is not limited to analyzing fluorescent measurements of hybridizations but may be readily utilized to analyze other measurements of hybridization.

For purposes of illustration, the present invention is described as being part of a computer system that designs a chip mask, synthesizes the probes on the chip, labels the nucleic acids, and scans the hybridized nucleic acid probes. Such a system is fully described in U.S. patent application Ser. No. 08/249,188, now U.S. Pat. No. 5,591,639 which has been incorporated by reference for all purposes. However, the present invention may be used separately from the overall system for analyzing data generated by such systems.

Figure 3:
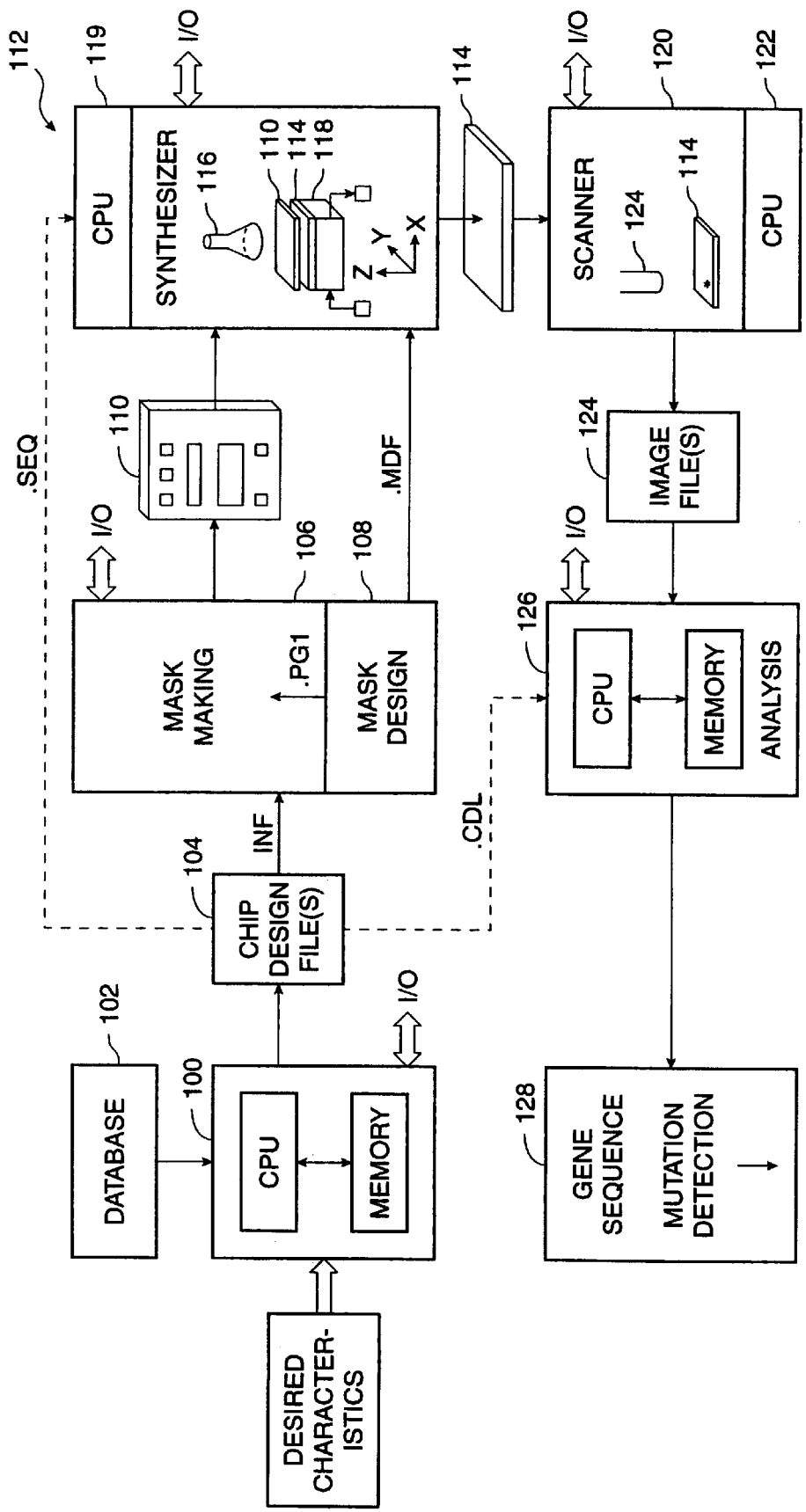
FIG. 3 illustrates an overall system for forming and analyzing arrays of biological materials such as DNA or RNA.

FIG. 3 illustrates a computerized system for forming and analyzing arrays of biological materials such as RNA or DNA. A computer 100 is used to design arrays of biological polymers such as RNA or DNA. The computer 100 may be, for example, an appropriately programmed Sun Workstation or personal computer or workstation, such as an IBM PC equivalent, including appropriate memory and a CPU as shown in FIGS. 1 and 2. The computer system 100 obtains inputs from a user regarding characteristics of a gene of interest, and other inputs regarding the desired features of the array. Optionally, the computer system may obtain information regarding a specific genetic sequence of interest from an external or internal database 102 such as GenBank. The output of the computer system 100 is a set of chip design computer files 104 in the form of, for example, a switch matrix, as described in PCT application WO 92/10092, and other associated computer files.

The chip design files are provided to a system 106 that designs the lithographic masks used in the fabrication of arrays of molecules such as DNA. The system or process 106 may include the hardware necessary to manufacture masks 110 and also the necessary computer hardware and software 108 necessary to lay the mask patterns out on the mask in an efficient manner. As with the other features in FIG. 1, such equipment may or may not be located at the same physical site, but is shown together for ease of illustration in FIG. 1. The system 106 generates masks 110 or other synthesis patterns such as chrome-on-glass masks for use in the fabrication of polymer arrays.

The masks 110, as well as selected information relating to the design of the chips from system 100, are used in a synthesis system 112. Synthesis system 112 includes the necessary hardware and software used to fabricate arrays of polymers on a substrate or chip 114. For example, synthesizer 112 includes a light source 116 and a chemical flow cell 118 on which the substrate or chip 114 is placed. Mask 110 is placed between the light source and the substrate/chip, and the two are translated relative to each other at appropriate times for deprotection of selected regions of the chip. Selected chemical reagents are directed through flow cell 118 for coupling to deprotected regions, as well as for washing and other operations. All operations are preferably directed by an appropriately programmed computer 119, which may or may not be the same computer as the computer(s) used in mask design and mask making.

The substrates fabricated by synthesis system 112 are optionally diced into smaller chips and exposed to marked receptors. The receptors may or may not be complementary to one or more of the molecules on the substrate. The receptors are marked with a label such as a fluorescein label (indicated by an asterisk in FIG. 1) and placed in scanning system 120. Scanning system 120 again operates under the direction of an appropriately programmed digital computer 122, which also may or may not be the same computer as the computers used in synthesis, mask making, and mask design. The scanner 120 includes a detection device 124 such as a confocal microscope or CCD (charge-coupled device) that is used to detect the location where labeled receptor (*) has bound to the substrate. The output of scanner 120 is an image file(s) 124 indicating, in the case of fluorescein labeled receptor, the fluorescence intensity (photon counts or other related measurements, such as voltage) as a function of position on the substrate. Since higher photon counts will be observed where the labeled receptor has bound more strongly to the array of polymers, and since the monomer sequence of the polymers on the substrate is known as a function of position, it becomes possible to determine the sequence(s) of polymer(s) on the substrate that are complementary to the receptor.

The image file 124 is provided as input to an analysis system 126 that incorporates the visualization and analysis methods of the present invention. Again, the analysis system may be any one of a wide variety of computer system(s), but in a preferred embodiment the analysis system is based on a Sun Workstation or equivalent. The present invention provides various methods of analyzing the chip design files and the image files, providing appropriate output 128. The present invention may further be used to identify specific mutations in a receptor such as DNA or RNA.

Figure 4:
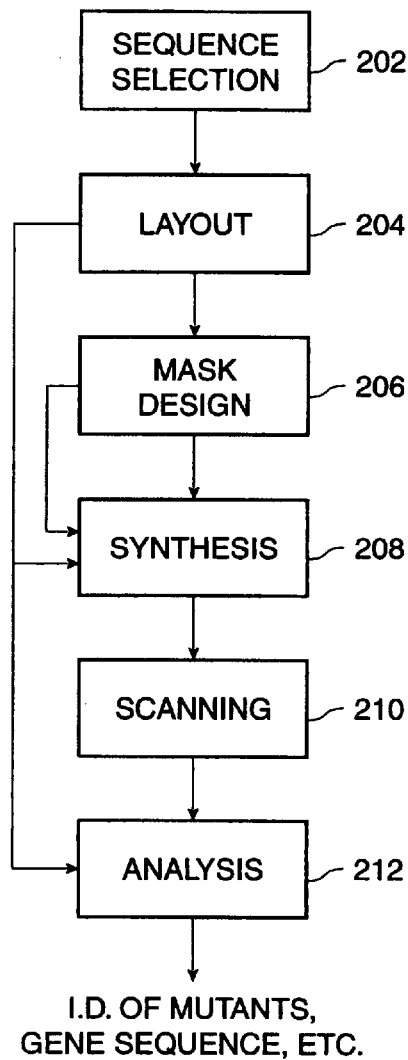
FIG. 4 is an illustration of the software for the overall system.

FIG. 4 provides a simplified illustration of the overall software system used in the operation of one embodiment of the invention. As shown in FIG. 4, the system first identifies the genetic sequence(s) or targets that would be of interest in a particular analysis at step 202. The sequences of interest may, for example, be normal or mutant portions of a gene, genes that identify heredity, or provide forensic information.

Sequence selection may be provided via manual input of text files or may be from external sources such as GenBank. At step 204 the system evaluates the gene to determine or assist the user in determining which probes would be desirable on the chip, and provides an appropriate "layout" on the chip for the probes. The chip usually includes probes that are complementary to a reference nucleic acid sequence which has a known sequence. A wild-type probe is a probe that will ideally hybridize with the reference sequence and thus a wild-type gene (also called the chip wild-type) would ideally hybridize with wild-type probes on the chip. The target sequence is substantially similar to the reference sequence except for the presence of mutations, insertions, deletions, and the like. The layout implements desired characteristics such as arrangement on the chip that permits "reading" of genetic sequence and/or minimization of edge effects, ease of synthesis, and the like.

Figure 5:
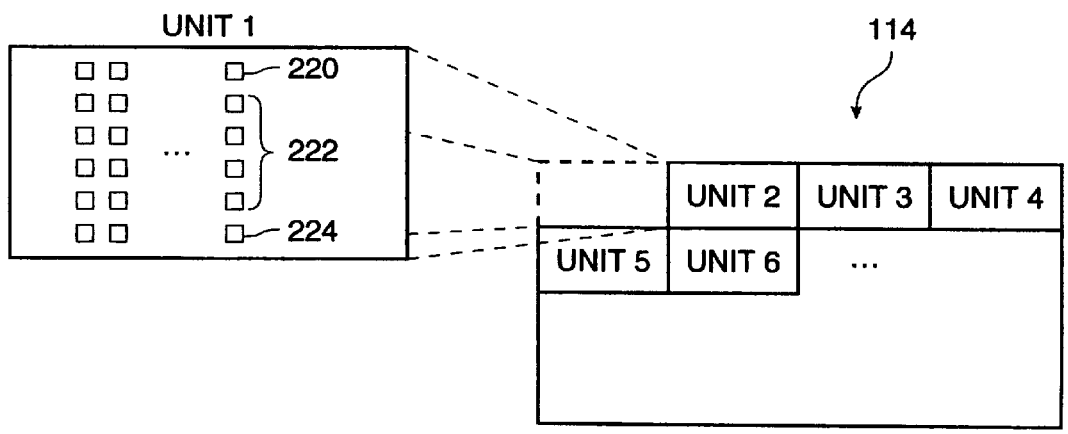
FIG. 5 illustrates the global layout of a chip formed in the overall system.

FIG. 5 illustrates the global layout of a chip. Chip 114 is composed of multiple units where each unit may contain different tilings for the chip wild-type sequence. Unit 1 is shown in greater detail and shows that each unit is composed of multiple cells which are areas on the chip that may contain probes. Conceptually, each unit is composed of multiple sets of related cells. As used herein, the term cell refers to a region on a substrate that contains many copies of a molecule or molecules of interest. Each unit is composed of multiple cells that may be placed in rows (or "lanes") and columns. In one embodiment, a set of five related cells includes the following: a wild-type cell 220, "mutation" cells 222, and a "blank" cell 224. Cell 220 contains a wild-type probe that is the complement of a portion of the wild-type sequence. Cells 222 contain "mutation" probes for the wild-type sequence. For example, if the wild-type probe is 3'-ACGT, the probes 3'-ACAT, 3'-ACCT, 3'-ACGT, and 3'-ACTT may be the "mutation" probes. Cell 224 is the "blank" cell because it contains no probes (also called the "blank" probe). As the blank cell contains no probes, labeled receptors should not bind to the chip in this area. Thus, the blank cell provides an area that can be used to measure the background intensity.

Again referring to FIG. 4, at step 206 the masks for the synthesis are designed. At step 208 the software utilizes the mask design and layout information to make the DNA or other polymer chips. This software 208 will control, among other things, relative translation of a substrate and the mask, the flow of desired reagents through a flow cell, the synthesis temperature of the flow cell, and other parameters. At step 210, another piece of software is used in scanning a chip thus synthesized and exposed to a labeled receptor. The software controls the scanning of the chip, and stores the data thus obtained in a file that may later be utilized to extract sequence information.

At step 212 a computer system according to the present invention utilizes the layout information and the fluorescence information to evaluate the hybridized nucleic acid probes on the chip. Among the important pieces of information obtained from DNA chips are the identification of mutant receptors and determination of genetic sequence of a particular receptor.

Figures 6, 7, 8:
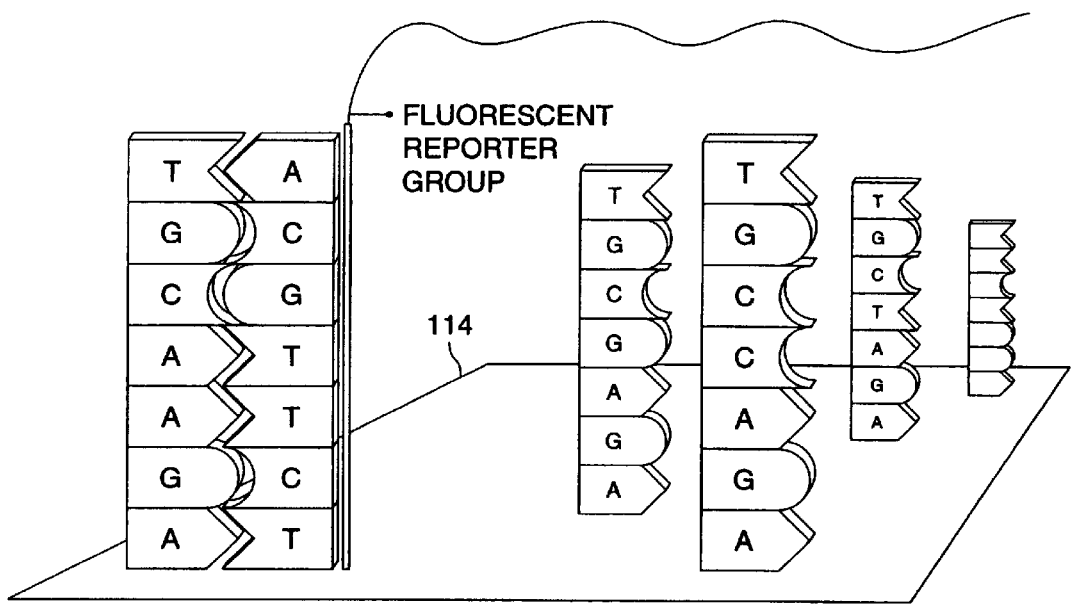
FIG. 6 illustrates conceptually the binding of probes on chips.
FIG. 7 illustrates probes arranged in lanes on a chip.
FIG. 8 illustrates a hybridization pattern of a target on a chip with a reference sequence as in FIG. 7.

FIG. 6 illustrates the binding of a particular target DNA to an array of DNA probes 114. As shown in this simple example, the following probes are formed in the array (only one probe is shown for the wild-type probe):

3'-AGAACGT
AGACCGT
AGAGCGT
AGATCGT

As shown, the set of probes differ by only one base so the probes are designed to determine the identity of the base at that location in the nucleic acid sequence.

When a fluorescein-labeled (or other marked) target with the sequence 5'-TCTTGCA is exposed to the array, it is complementary only to the probe 3'-AGAACGT, and fluorescein will be primarily found on the surface of the chip where 3'-AGAACGT is located. Thus, for each set of probes that differ by only one base, the image file will contain four fluorescence intensities, one for each probe. Each fluorescence intensity can therefore be associated with the base of each probe that is different from the other probes. Additionally, the image file will contain a "blank" cell which can be used as the fluorescence intensity of the background. By analyzing the five fluorescence intensities associated with a specific base location, it becomes possible to extract sequence information from such arrays using the methods of the invention disclosed herein.

FIG. 7 illustrates probes arranged in lanes on a chip. A reference sequence is shown with five interrogation positions marked with number subscripts. An interrogation position is a base position in the reference sequence where the target sequence may contain a mutation or otherwise differ from the reference sequence. The chip may contain five probe cells that correspond to each interrogation position. Each probe cell contains a set of probes that have a common base at the interrogation position. For example, at the first interrogation position, $I_1$, the reference sequence has a base T. The wild-type probe for this interrogation position is 3'-TGAC where the base A in the probe is complementary to the base at the interrogation position in the reference sequence.

Similarly, there are four "mutant" probe cells for the first interrogation position, $I_1$. The four mutant probes are 3'-TGAC, 3'-TGCC, 3'-TGGC, and 3'-TGTC. Each of the four mutant probes vary by a single base at the interrogation position. As shown, the wild-type and mutant probes are arranged in lanes on the chip. One of the mutant probes (in this case 3'-TGAC) is identical to the wild-type probe and therefore does not evidence a mutation. However, the redundancy gives a visual indication of mutations as will be seen in FIG. 8.

Still referring to FIG. 7, the chip contains wild-type and mutant probes for each of the other interrogation positions $I_2$–$I_5$. In each case, the wild-type probe is equivalent to one of the mutant probes.

FIG. 8 illustrates a hybridization pattern of a target on a chip with a reference sequence as in FIG. 7. The reference sequence is shown along the top of the chip for comparison. The chip includes a WT-lane (wild-type), an A-lane, a C-lane, a G-lane, and a T-lane (or U). Each lane is a row of cells containing probes. The cells in the WT-lane contain probes that are complementary to the reference sequence. The cells in the A-, C-, G-, and T-lanes contain probes that are complementary to the reference sequence except that the named base is at the interrogation position.

In one embodiment, the hybridization of probes in a cell is determined by the fluorescent intensity (e.g., photon counts) of the cell resulting from the binding of marked target sequences. The fluorescent intensity may vary greatly among cells. For simplicity, FIG. 8 shows a high degree of hybridization by a cell containing a darkened area. The WT-lane allows a simple visual indication that there is a mutation at interrogation position $I_4$ because the wild-type cell is not dark at that position. The cell in the C-lane is darkened which indicates that the mutation is from T→G (mutant probe cells are complementary so the C-cell indicates a G mutation).

In practice, the fluorescent intensities of cells near an interrogation position having a mutation are relatively dark creating "dark regions" around a mutation. The lower fluorescent intensities result because the cells at interrogation positions near a mutation do not contain probes that are perfectly complementary to the target sequence; thus, the hybridization of these probes with the target sequence is lower. For example, the relative intensity of the cells at interrogation positions $I_3$ and $I_5$ may be relatively low because none of the probes therein are complementary to the target sequence. Although the lower fluorescent intensities reduce the resolution of the data, the methods of the present invention provide highly accurate base calling within the dark regions around a mutation and are able to identify other mutations within these regions.

The present invention calls bases by assigning the bases the following codes:

| Code | Group | Meaning |
| --- | --- | --- |
| A | A | Adenine |
| C | C | Cytosine |
| G | G | Guanine |
| T | T(U) | Thymine (Uracil) |
| M | A or C | aMino |
| R | A or G | puRine |
| W | A or T(U) | Weak interaction (2 H bonds) |
| Y | C or T(U) | pYrimidine |
| S | C or G | Strong interaction (3 H bonds) |
| K | G or T(U) | Keto |
| V | A, C or G | not T(U) |
| H | A, C or T(U) | not G |
| D | A, G or T(U) | not C |
| B | C, G or T(U) | not A |
| N | A, C, G, or T(U) | Insufficient intensity to call |
| X | A, C, G, or T(U) | Insufficient discrimination to call |

Most of the codes conform to the IUPAC standard. However, code N has been redefined and code X has been added.

II. Probability Base Calling Method

The probability base calling method is a method of calling bases in a sample nucleic acid sequence which provides extremely high accuracy. At the same time, confidence information is provided that indicates the likelihood that the base has been called correctly. The probability base calling method is robust and uniformly optimal regardless of the experimental conditions.

For simplicity, the probability base calling method will be described as being used to identify one unknown base in a sample nucleic acid sequence. In practice, the method is typically used to identify many or all the bases in a nucleic acid sequence or sequences.

In a preferred embodiment, the unknown base will be identified by evaluation of up to four mutation probes. For example, suppose a gene of interest has the DNA sequence of 5'-AGAACCTGC-3' with a possible mutation at the underlined base position. Suppose that 5-mer probes are to be synthesized for the chip. A representative wild-type probe of 5'-TTGGA is complementary to the region of the sequence around the possible mutation. The "mutation" probes will be the same as the wild-type probe except for a different base at the third position as follows: 3'-TTAGA, 3'-TTCGA, 3'-TTGGA, and 3'-TTTGA.

If the fluorescently marked sample sequence is exposed to the above four mutation probes, the intensity should be highest for the probe that binds most strongly to the sample sequence. Therefore, if the probe 3'-TTTGA shows the highest intensity, the unknown base in the sample will generally be called an A mutation because the probes are complementary to the sample sequence. Although calling bases according to the highest intensity probe is satisfactory in some instances, the accuracy may be affected by many experimental conditions.

Figure 9:
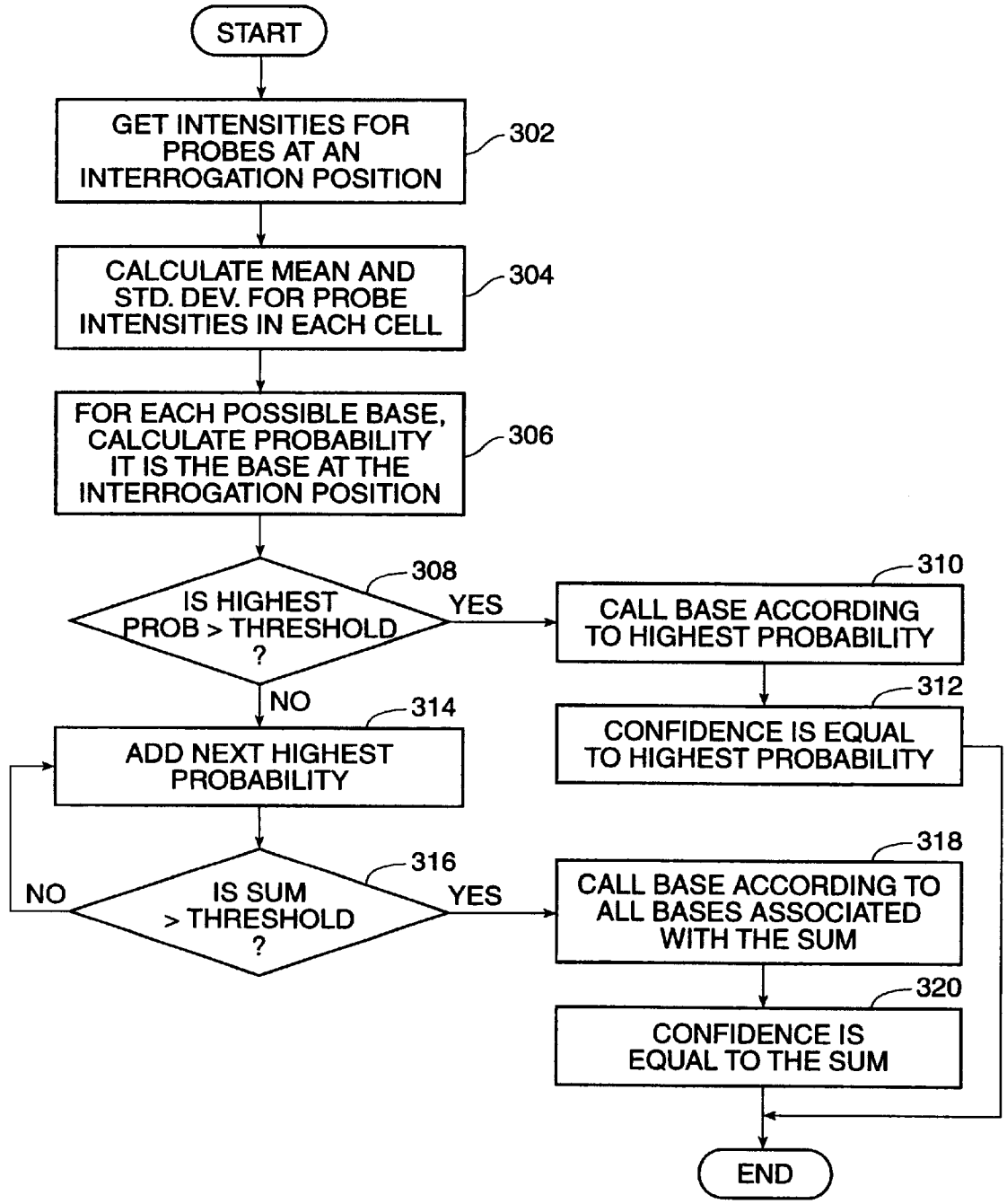
FIG. 9 illustrates the high level flow of the probability base calling method.

FIG. 9 shows the high level flow of the probability base calling method. At step 302, the system retrieves the intensities for probes at an interrogation position. Although not necessary, the background intensity (e.g., from the blank cell) may be subtracted from each of the observed intensities. If a DNA sequence is being called, the system may loop through the flowchart for each base position to be called in the sequence. For simplicity, FIG. 9 shows the method of calling a base at a single interrogation position in the sample sequence.

As discussed earlier, each cell on the chip defines an area which contains a set of identical probes. After the chip has been exposed to a fluorescein-labeled (or other marked) sample sequence, intensity readings are taken. Intensity readings are taken over the surface of the cell resulting in multiple intensity readings for each cell. The system calculates the mean and standard deviation for the intensities measured for each cell at step 304. As each cell is associated with a probe type, the term "probe intensity" will generally refer to the mean of intensities associated with the probe. Although the mean is utilized in the preferred embodiment, other statistical analysis could be used including an average.

At step 306, the system calculates the probability that each base (e.g., A, C, G, or T(U)) is at the interrogation position. If we assume that the base associated with the probe having the highest probe intensity (i.e., best hybridizes with the sample sequence) is the correct call, the probability that the unknown base is a certain base is equal to the following:

$$\text{Prob } (X) = \text{Prob } (I_x > \max (I_y))_{y \ne x} \tag{1}$$

where X and Y are A, C, G, or T(U); I is the probe intensity associated with the subscripted base; and max represents the maximum of the probe intensities. Thus, the probability that a base at an interrogation position is base A is the probability that the probe intensity associated with base A (i.e., has A's complement T) is greater than the highest probe intensity associated with C, G, and T.

The probability that the probe intensity associated with base A is greater than the highest probe intensity associated with the other bases is approximated by the following:

$$\text{Prob}(I_X > \max(I_Y)) \approx \frac{\prod \text{Prob}(I_X > I_Y)_{Y \ne X}}{\sum_{Z=A,C,G,T} \prod \text{Prob}(I_Z > I_Y)_{Y \ne Z}} \tag{2}$$

where X, Y and Z are A, C, G, or T(U) and Π represents the product of the probabilities that $I_x$ is greater than each of the other possible bases. Thus, the probability that a base at an interrogation position is base A is proportional to the product of the probabilities that the probe intensity associated with base A is greater than the probe intensities associated with C, G, and T. In a preferred embodiment, the system normalizes the probabilities so that the sum of the probabilities equals 1. As shown above, the system accomplishes this by dividing each probability by the sum of the probabilities associated with the different bases.

According to the present invention, the probability that a probe intensity associated with a base is greater than the probe intensity associated with another base is as follows:

$$\text{Prob}(I_X > I_Y) = \Phi\left(\frac{I_X - I_Y}{\sqrt{\sigma_X^2 - \sigma_Y^2}}\right)_{Y \ne X} \tag{3}$$

where X and Y are A, C, G, or T(U) and a represents the standard deviation ($\sigma^2$ being the variance) of the intensities measured for the cell associated with the subscripted base. The Φ function is as follows:

$$\Phi(X) = \int_{-\infty}^{X} \frac{1}{\sqrt{2\pi}} e^{-\frac{y^2}{2}} dy \tag{4}$$

which represents the density equation of standard normal distribution and may be determined by many number of methods known to those skilled the art.

Utilizing these equations, the system calculates the probability that the base at the interrogation position is A, the probability that the base at the interrogation position is C, the probability that the base at the interrogation position is G, the probability that the base at the interrogation position is T(U). In a preferred embodiment, probabilities are normalized so that the sum of these probabilities equals 1.

At step 308, the system determines if the highest probability associated with a base is greater than a probability threshold. In one embodiment, the value for the probability threshold is 0.8 (for probabilities that have been normalized). The probability threshold is a user defined value that determines the threshold that a probability should cross before the base is called. If the probabilities are normalized so that their sum is equal to 1, the probability threshold will be in the range of 0.25 to 1.0. The use of a probability threshold is not necessary but allows the user to select the confidence of the resulting base calls. It should be noted that a probability threshold of 0.25 corresponds to calling the base associated with the highest probability (i.e., no threshold).

If the highest probability is greater than the probability threshold, the system calls the base as the base associated with the highest probability at step 310. Thus, if the probes in the G-lane cell had the highest probability and the probability is greater than the probability threshold, the system would call the base at the interrogation position a C since the probes are complementary to the sample sequence. At step 312, the confidence (i.e., the likelihood that the base is called correctly) is set equal to the highest probability.

At step 314, the system creates a sum of probabilities by adding the highest probability to the next highest probability. The sum represents the probability that the base is either of the bases associated with the two highest probabilities. The system then determines if the sum is greater than the probability threshold at step 316. If the sum is greater than the probability threshold, the system calls the base as an ambiguity code representing the bases that are associated with two highest probabilities. Thus, if the probabilities associated with bases A and C the two highest probabilities and their sum is greater than the probability threshold, the system would call the base at the interrogation position an M (meaning A or C). Since the probes are complementary to the sample sequence, the probabilities associated with bases A and C are the probabilities of the probes in the T- and G-lane cells, respectively. At step 320, the confidence is set equal to the sum of the probabilities that exceed the probability threshold.

If the sum is not greater than the probability threshold, the system adds the next highest probability to the sum of probabilities at 314 and the sum is compared to the probability threshold at step 316. When the sum is greater than the probability threshold, the system calls the base as an ambiguity code representing all the bases that are associated with probabilities included in the sum. As before, the confidence is set equal to the sum of the probabilities that exceed the probability threshold.

As an example of the probability base calling method, suppose a known nucleic acid sequence 5'-ACTGTAGGG is to be called. After the sequence is labeled and exposed to a DNA chip, an image file is generated that has the fluorescent intensities (e.g., photon counts) associated with each cell on the chip. The mean and standard deviation are calculated and are as follows for each interrogation position:

| IntPos | Mean A | Mean C | Mean G | Mean T |
|---|---|---|---|---|
| 1 | 176.8 | 65.9 | 73.4 | 51.7 |
| 2 | 57.9 | 119.2 | 60.5 | 56.5 |
| 3 | 53.9 | 60.2 | 54.8 | 81.3 |
| 4 | 55.1 | 53.9 | 76.0 | 56.0 |
| 5 | 50.8 | 52.3 | 53.1 | 59.0 |
| 6 | 54.4 | 53.0 | 52.6 | 51.2 |
| 7 | 50.9 | 51.8 | 52.5 | 51.6 |
| 8 | 52.1 | 53.2 | 53.4 | 50.7 |
| 9 | 51.1 | 50.9 | 51.1 | 50.8 |

| IntPos | StDev A | StDev C | StDev G | StDev T |
|---|---|---|---|---|
| 1 | 18.2 | 8.3 | 11.4 | 5.0 |
| 2 | 8.1 | 18.1 | 10.5 | 6.2 |
| 3 | 6.8 | 9.2 | 5.8 | 16.6 |
| 4 | 5.6 | 6.7 | 12.6 | 8.0 |
| 5 | 5.4 | 5.0 | 5.7 | 8.8 |
| 6 | 5.8 | 5.5 | 5.7 | 4.7 |
| 7 | 6.1 | 5.8 | 6.4 | 5.9 |
| 8 | 5.1 | 5.6 | 5.5 | 6.1 |
| 9 | 6.1 | 6.1 | 5.9 | 6.2 |

The mean and standard deviations above represent the complements to the chip cell. For example, the mean and standard deviation for A were determined from the intensities associated with the cell that contained probes having the base T at the interrogation position.

These means and standard deviations were utilized to produce the following probabilities according to the equations set forth above:

| IntPos | Prob A | Prob C | Prob G | Prob T |
|---|---|---|---|---|
| 1 | 1 | 0 | 5.2e-7 | 0 |
| 2 | 2.3e-4 | 1 | 9.2e-4 | 8.9e-5 |
| 3 | 0.01 | 0.077 | 0.013 | 0.9 |
| 4 | 0.019 | 0.013 | 0.93 | 0.033 |
| 5 | 0.056 | 0.11 | 0.16 | 0.68 |
| 6 | 0.42 | 0.25 | 0.22 | 0.11 |
| 7 | 0.18 | 0.26 | 0.33 | 0.24 |
| 8 | 0.21 | 0.32 | 0.35 | 0.12 |
| 9 | 0.26 | 0.24 | 0.26 | 0.23 |

The probabilities have been normalized so that the sum of the probabilities associated with the bases at each interrogation position equals 1.

If the bases are called according to the highest probability (also equal to a threshold of 0.25 in this case), the bases would be called as follows with the associated confidence:

| IntPos | BaseCall | Confid |
|---|---|---|
| 1 | A | 1 |
| 2 | C | 1 |
| 3 | T | 0.9 |
| 4 | G | 0.93 |
| 5 | T | 0.68 |
| 6 | A | 0.42 |
| 7 | G | 0.33 |
| 8 | G | 0.35 |
| 9 | G | 0.26 |

As the sample nucleic acid was known to be 5'-ACTGTAGGG, the sequence was correctly called by the base probability method. Importantly, the confidence values indicate the likelihood that each base call is correct.

If the bases are called with a probability threshold of 0.5, the bases would be called as follows:

| IntPos | Basecall | Confid |
|---|---|---|
| 1 | A | 1 |
| 2 | C | 1 |
| 3 | T | 0.9 |
| 4 | G | 0.93 |
| 5 | T | 0.68 |
| 6 | M | 0.67 |
| 7 | S | 0.59 |
| 8 | S | 0.67 |
| 9 | R | 0.52 | where the ambiguity codes M=A or C, S=C or G and R=A or G according to the IUPAC codes. As shown, all the confidence values are above 50% for each base call.

Advantages of the probability base calling method include that it is extremely accurate in calling bases of sample nucleic acid sequences and provides a confidence value of the accuracy of the base call. The method is robust and uniformly optimal regardless of experimental conditions. Additionally, the probability base calling method is capable of accurately calling bases and identifying mutations near other mutations.

III. Maximum Probability Method

The present invention provides a maximum probability method of increasing the accuracy of base calling by analyzing multiple experiments preformed on a DNA or RNA molecule. The multiple experiments may be repetitions of the same experiment or may vary by the number of probes on the chip, wash (or salt) concentration, tiling method, and the like. Additionally, the multiple experiments may include experiments preformed on the sense and anti-sense strands of the sample nucleic acid sequence. Although in a preferred embodiment, this method is performed in conjunction with probability base calling, the method may be readily used with other base calling methods including those disclosed in U.S. patent application Ser. No. 08/327,525.

Figure 10:
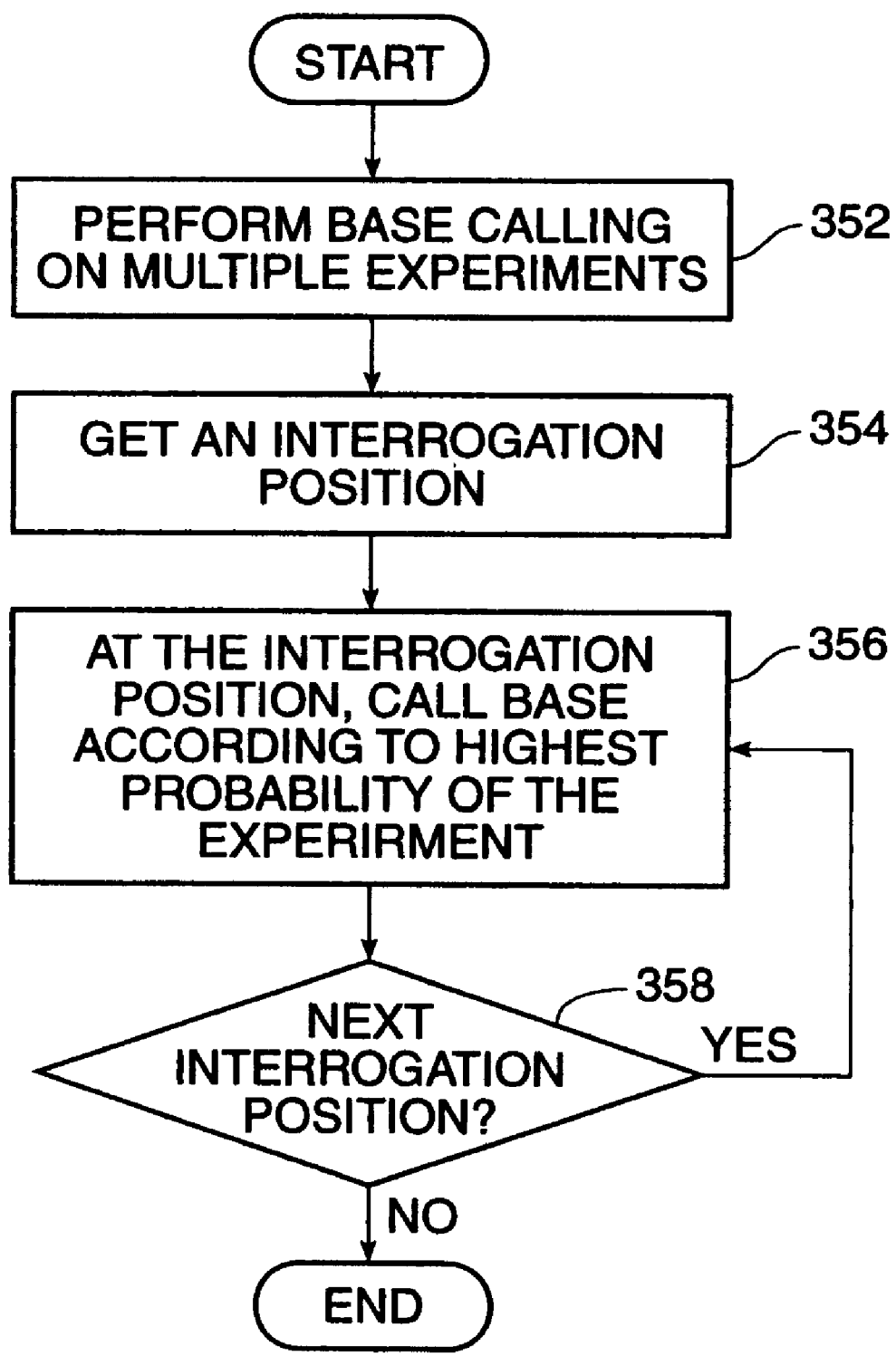
FIG. 10 illustrates the flow of the maximum probability method.

FIG. 10 shows the flow of the maximum probability method. The method will be described as sequencing a sample nucleic acid sequence. At step 352, base calling is performed on data from multiple experiments on the sample nucleic acid sequence.

The system identifies an interrogation position in the sample nucleic acid sequence at step 354. The system then identifies the base that was called with the highest probability among the multiple experiments. In a preferred embodiment, the highest probability is determined by the probability base calling method. In other embodiments, for example, the base that had the highest associated intensity may be identified. At step 356, the system calls the base at the interrogation position as the base with the highest probability. The probability also represents the confidence that the base has been called correctly.

At step 358, the system determines if base calling should be performed on another interrogation position. If so, the system proceeds to step 354 to retrieve the next interrogation position.

As an example, six known nucleic acid sequence clones of HIV DNA were labeled and exposed to the HIV418 chip available from Affymetrix, Inc., Santa Clara, Calif. The multiple experiments for each HIV clone included sequencing the sense and anti-sense strands of the HIV clone. The following shows the percentage error of probability base calling for the sense and anti-sense strands of the HIV clones:

| HIV Clone | Sense | Anti-sense | MaxProb |
|---|---|---|---|
| 4 mut 18 | 3.08 | 1.83 | 1.73 |
| HXB | 2.02 | 1.44 | 1.35 |
| NY5 | 2.31 | 1.44 | 1.63 |
| NY5-215 | 2.60 | 1.15 | 1.25 |
| NY5-5mut | 2.88 | 1.54 | 1.44 |
| pPol19 | 3.17 | 2.98 | 1.83 |
| Average | 2.68 | 1.73 | 1.54 |

As shown, the probability base calling method had a 3.08 percent error for sequencing the bases of the 4 mut 18 sense strand. The probability base calling method had a 1.83 percent error for sequencing the bases of the 4 mut 18 anti-sense strand. However, if the maximum probability method is utilized, the error percentage drops to 1.73. More significantly, the table above shows that the average of the error percentages reveals that the maximum probability method provides a 1.54 percent error—which translates to a 98.46 percent correct base calling. This percentage is a significant improvement over present day chip sequencing methods.

The maximum probability method provides a significant improvement in base calling correctness by advantageously combining the results from multiple experiments. Although the method has been described as sequencing a sample nucleic acid sequence, the method may be utilized to sequence genes or call individual bases.

IV. Product of Probabilities Method

The present invention provides a product of probabilities method of increasing the accuracy of base calling by analyzing multiple experiments preformed on a DNA or RNA molecule. The multiple experiments may be repetitions of the same experiment or may vary by the number of probes on the chip, wash (or salt) concentration, tiling method, and the like. Additionally, the multiple experiments may include experiments preformed on the sense and anti-sense strands of the sample nucleic acid sequence. Although in a preferred embodiment, this method is performed in conjunction with probability base calling, the method may be readily used with other base calling methods including those disclosed in U.S. patent application Ser. No. 08/327,525.

Figure 11:
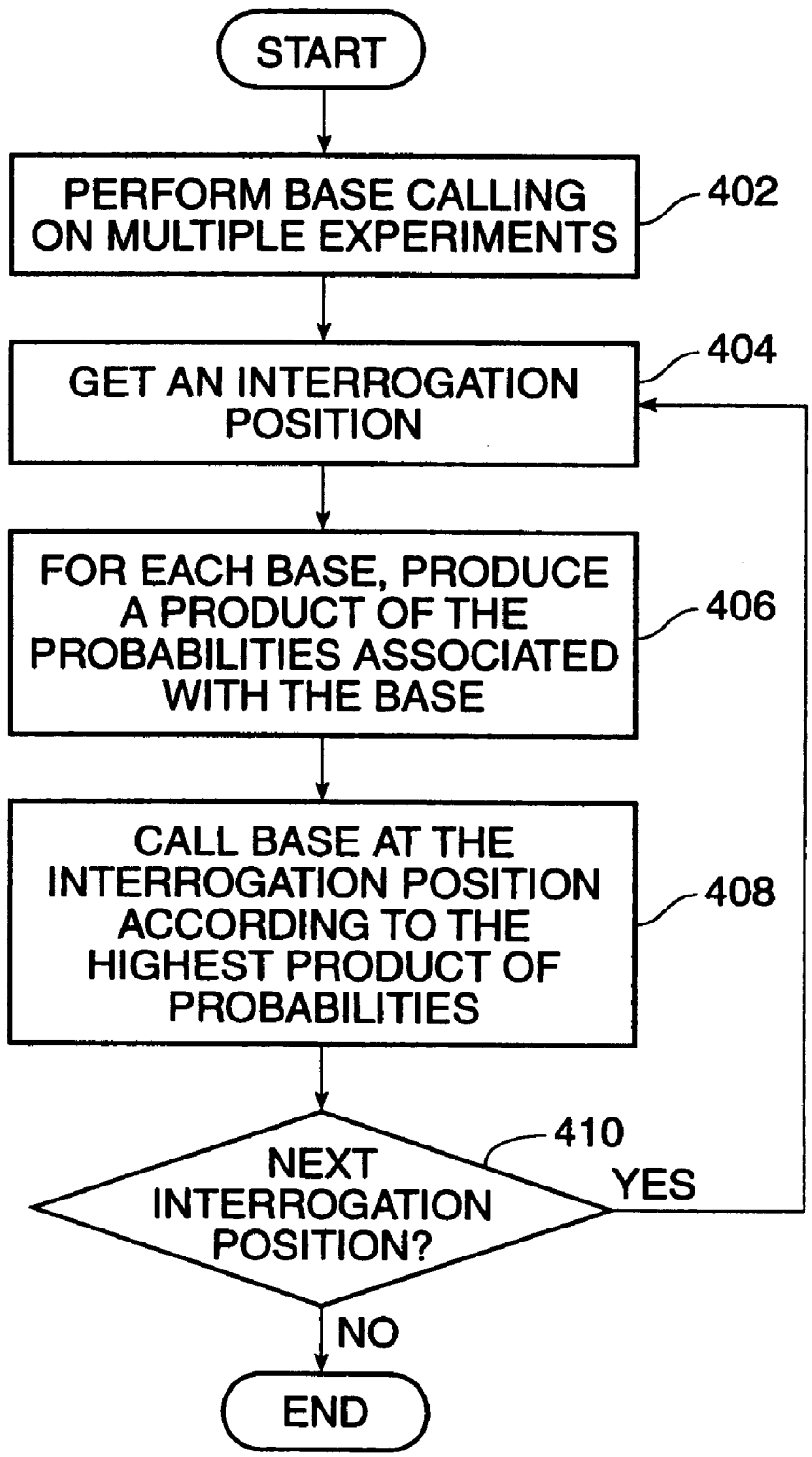
FIG. 11 illustrates the flow of the product of probabilities method.

FIG. 11 shows the flow of the product of probabilities method. The method will be described as sequencing a sample nucleic acid sequence. At step 402, base calling is performed on data from multiple experiments on the sample nucleic acid sequence.

The system identifies an interrogation position in the sample nucleic acid sequence at step 404. The system then multiplies the probabilities associated with each base among the experiments to produce a product at step 406. For example, the system identifies the probability that the base at the interrogatory position is base A from each experiment. The system multiplies each of these percentages to produce a product of probabilities for A. The system similarly produces a product of probabilities for C, G and T. Optionally, the system then normalizes each of the product of probabilities by dividing each by the sum of the products of probabilities for A, C, G, and T. In this way, the sum of the resulting products of probabilities will equal 1.

In a preferred embodiment, the highest probability is determined by the probability base calling method. In other embodiments, for example, the base that had the highest associated intensity may be identified. At step 408, the system calls the base at the interrogation position as the base with the highest product of probabilities.

At step 410, the system determines if base calling should be performed on another interrogation position. If so, the system proceeds to step 404 to retrieve the next interrogation position.

The product of probabilities method provides a significant improvement in base calling correctness by advantageously combining the results from multiple experiments. Although the method has be described as sequencing a sample nucleic acid sequence, the method may be utilized to sequence genes or call individual bases.

V. Wild-Type Base Preference Method

The present invention provides methods of increasing the accuracy of base calling by analyzing both strands of a DNA (or complementary strands of RNA) molecule and calling the base according to the chip wild-type base. The accuracy is improved because some bases are correctly identified more often depending on the wild-type base on the chip. By analyzing both strands of the DNA molecule, the base calling method can better utilize this information to improve the accuracy of base calling. In a preferred embodiment, this method is performed in conjunction with probability base calling but others may be utilized.

A molecule of DNA is composed of two complementary strands of deoxyribonucleotides (bases). Before the sequence of the DNA is evaluated, the DNA molecule is cleaved into its two complementary strands. One strand is then cloned to produce enough nucleic acid sequences to be labeled and sequenced (called) according to the methods disclosed herein. For identification purposes, this strand of DNA will be called the "sense" strand.

According to the present invention, the other strand, the "anti-sense" strand, is also cloned, labeled, and sequenced. Through analysis of known nucleic acid sequences, it has been determined that when the wild-type base at the interrogation position on the chip is A or G, the resulting base call is correct a higher percentage of the time. Conversely, it has been determined that when the wild-type base at the interrogation position on the chip is C or T, the resulting base call is incorrect a higher percentage of the time. For example, when the wild-type base at the interrogation position on the chip is T, the resulting base call is incorrect (i.e., the base is miscalled) up to three times more often than the other chip wild-type bases.

It is believed that some of the inaccuracy may be caused by the fluorescein label which is bound to the base thymine in some embodiments. Additionally, some of the inaccuracy may be caused by the fact that both C and T are pyrimidines. Whatever the cause, this information is utilized to increase the accuracy of base calling methods.

As the sense and anti-sense nucleic acid strands are complementary, the base calling method should indicate complementary bases for the two strands. For example, if the sense strand has a base A at an interrogation position, the base calling method should indicate the base is A. However, the anti-sense strand will have a base T at a corresponding interrogation position, so the base calling method should indicate the base is T.

Figure 12:
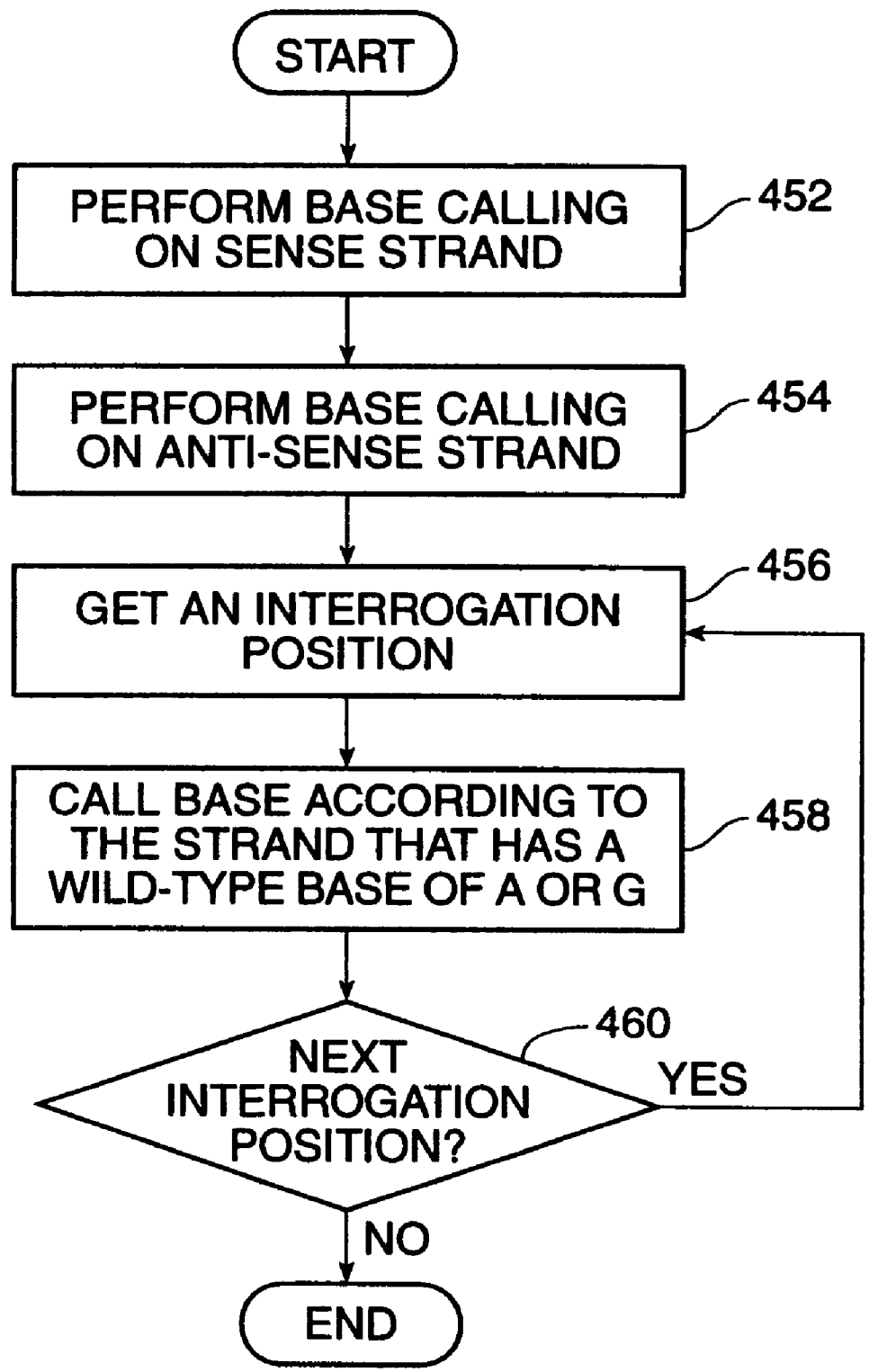
FIG. 12 illustrates the flow of the wild-type base preference method.

FIG. 12 illustrates the flow of the wild-type base preference method. At step 452, base calling is performed on the sense strand to call a base at an interrogation position in the sense strand. Base calling is performed on the anti-sense strand to call the base at the interrogation position in the sense strand at step 454. The sense and anti-sense strands may be analyzed separately or concurrently.

The system identifies an interrogation position in the sample nucleic acid sequence at step 456. At step 458, the system calls the base at the interrogation position according to the strand that has a chip wild-type base A or G at the interrogation position. Thus, if the anti-sense strand chip wild-type at the interrogation position is G, the base is called according to the anti-sense strand.

As an example, assume the base call utilizing the sense strand calls the base at the interrogation position is an A. Assume also the base call utilizing the anti-sense strand calls the base at the interrogatory position a C (which translates to a G for the sense strand as the sense and anti-sense strands are complementary). If the chip wild-type base for the sense strand is A (which means the chip wild-type base for the anti-sense strand is T), the system calls the base an A according to the base call that utilizes the sense strand because the chip wild-type associated with the sense strand is an A or G.

At step 460, the system determines if base calling should be performed on another interrogation position. If so, the system proceeds to step 456 to retrieve the next interrogation position.

Although the wild-type base preference method has been described as giving a higher priority to A and G as the chip wild-type, other bases may be preferred in other embodiments. Accordingly, the method is not limited to preference of any specific chip wild-type bases.

VI. Software Appendix

The Software appendix (copyright Affymetrix, Inc.) provide C++ source code for implementing the present invention. The source code is written for a Sun Workstation.

The above description is illustrative and not restrictive. Many variations of the invention will become apparent to those of skill in the art upon review of this disclosure. Merely by way of example, while the invention is illustrated with particular reference to the evaluation of DNA (natural or unnatural), the methods can be used in the analysis from chips with other materials synthesized thereon, such as RNA. The scope of the invention should, therefore, be determined not with reference to the above description, but instead should be determined with reference to the appended claims along with their full scope of equivalents.

27
APPENDIX

```
#ifndef StandardUnitClass_HEADER
define StandardUnitClass_HEADER include <fstream.h>
include <Inputs.h>
#include <AtomClass.h>
#include <UnitClass.h>
#include <ResultsClass.h>

////////////////////////////////////////////////////////////////
//
// Class:       StandardUnitClass
//
// Description: Stores data for a standard tilied unit of a chip.
//
// Members:
//    Private:
//
//       ComputeStatRatios      - Statistical mismatch ratios.
//       ComputeRefRatios       - Reference mismatch ratios.
//       ComputeStanRatios      - Compute intensity mismatch ratios.
//       ComputeProbabilities   - Compute the probability of ACGT being the
//                                correct call.
//       ComputeWTSeq           - Compute WT sequence.
//       ComputeStanUnknownSeq  - Compute unknown sequence. (standard)
//       ComputeStatUnknownSeq  - Compute unknown sequence. (statistic)
//       ComputeAtomData        - Compute atom data.
//       BaseFirstRatio         - Determines called base code based on
//                                base with highest intensity.
//       BaseSecondRatio        - Determines called base code based on
//                                bases with two highest intensity.
//       BaseThirdRatio         - Determines called base code based on
//                                bases with three highest intensity.
//
//    Public:
//
//       ProcessUnitData        - Compute data for unit.
//       OutputUnitData         - Output data for unit.
//       ReadUnitStats          - Statistical data read.
//       ComputeAmbiguityData   - Compute ambiguity data.
//
//       ComputeRefUnknownSeq   - Compute unknown sequence. (reference)
//       ComputeProbUnknownSeq  - Compute unknown sequence. (Probability)
//
//       StandardUnitClass      - Constructor.
//       -StandardUnitClass     - Destructor.
//
// Notes:
//
////////////////////////////////////////////////////////////////
class StandardUnitClass : public UnitClass , public ResultsClass { private:

void ComputeStatRatios();
    void ComputeRefRatios();
    void ComputeStanRatios();
    void ComputeProbabilities();

void ComputeWTSeq();
    void ComputeStanUnknownSeq();
    void ComputeStatUnknownSeq();
    void ComputeProbUnknownSeq();
```

28

```
    char BaseFirstRatio(CodeType *, AtomClass *);
    char BaseSecondRatio(CodeType *, AtomClass *);
    char BaseThirdRatio(CodeType *, AtomClass *);

char BaseFirstRatio(CodeType *, int *, AtomClass *);
    char BaseSecondRatio(CodeType *, int *, AtomClass *);
    char BaseThirdRatio(CodeType *, int *, AtomClass *);

char BaseFirstRatio(CodeType *, char);
    char BaseSecondRatio(CodeType *, char, char);

public:

void ProcessUnitData(int);
    void SaveUnitDataOne();
    void SaveUnitDataTwo();
    void LoadUnitDataOne(int);
    void LoadUnitDataTwo(int);
    void ReadUnitStats(char *, ifstream &, int);
    void OutputUnitData(int);

void ComputeAmbiguityData(char * =NULL, char * =NULL);
    void ComputeCalledCode();
    void ComputeAtomData(int);
    void ComputeRefUnknownSeq(StandardUnitClass *);
    void ReComputeRefUnknownSeq(StandardUnitClass *);
    void ScreenAmbiguityData(StandardUnitClass *);

void PadUnit(int *);

StandardUnitClass();
    StandardUnitClass(int, int, InputClass *);
    ~StandardUnitClass();
};
////////////////////////////////////////////////////////////////
endif ifndef ROUTINE_HEADER
define ROUTINE_HEADER

////////////////////////////////////////////////////////////////
//
// Description: Statistical functions.
//
// Functions:
//      varIx_Iy       - Calculate the variance of Ix-Iy.
//      Z              - Calculate the Z-value of x.
//      PHI            - Calculate the Phi-function of X
//                       (probability in a normal distribution).
//
//////////////////////////////////////////////////////////////// float varIx_Iy(float STDx, float STDy);
float Z(float x);
float PHI(float X);

////////////////////////////////////////////////////////////////
endif
```

```
#ifndef ResultsClass_HEADER
define ResultsClass_HEADER include <MeanStdv.h>
include <AtomClass.h>
#include <Inputs.h>
////////////////////////////////////////////////////////////////////////
//
// Class:       ResultsClass
//
// Description: Stores all unit results.
//
// Members:
//    Protected:
//
//       RCNumAtoms           - Number of atoms.
//       NumAmbiguities       - Number of ambiguities.
//       WTSeq                - Wild type sequence.
//       MutWTSeq             - Mutation wild type sequence.
//       CalledSeq            - Called sequence based on inten ratios.
//       CalledSeqConf        - Confidence of each base call.
//       MutCalledSeq         - Mutation called sequence (optimize)
//       RRCalledSeq          - Second iteration called sequence.
//       NumAtoms             - Number of atoms in unit.
//       AmbigSum             - Ambiguity code counts.
//       CalledCode           - Called sequence codes.
//       Ratios               - Mismatch ratios.
//       CalledRatio          - Ratio used for final call (for ratio method)
//       Probabilities        - Probabilities of ACGT being the correct call.
//
//    Public:
//
//       GetCalledCode        - Return atom called code.
//       GetRatios            - Return atom reference ratios.
//       GetProbabilities     - Return atom probabilities.
//
//       GetWTSeq             - Return ith base of wildtype sequence.
//       GetMutWTSeq          - Return ith base of mutation wt sequence.
//       GetCalledSeq         - Return ith base of called sequence.
//       GetCalledSeqConf     - Return ith base's confidence.
//       GetMutCalledSeq      - Return ith base of mutation sequence.
//
//       OutputWTSeq          - Output unit wildtype sequence to file
//       OutputCalledSeq      - Output unit called sequence to file.
//       OutputSummaryData    - Output unit summary data to file.
//       OutputIntensityData  - Output unit intensity data to file.
//       OutputAmbiguityData  - Output unit ambiguity data to file.
//       OutputRatioData      - Output unit ratio data.
//       OutputCalledRatioData - Output unit called ratio data.
//       OutputProbabilityData - Output unit probability data.
//       OutputAmbiguityData  - Output unit ambiguity data to file.
//       OutputAmbiguityCells - Output unit ambiguity cells to file.
//       OutputStatAnalysisData - Output unit statistical analysis data.
//       OutputStanAnalysisData - Output unit statistical analysis data.
//
//       ResultsClass         - Constructor.
//       ~ResultsClass        - Destructor.
//
// Notes:
//
////////////////////////////////////////////////////////////////////////
class ResultsClass {
```

30

```
protected:
    int RCNumAtoms;
    int NumAmbiguities;

InputClass *In;

AtomClass *RCAtomData;

CharArrayClass WTSeq;
    CharArrayClass MutWTSeq;
    CharArrayClass CalledSeq;
    CharArrayClass MutCalledSeq;
    CharArrayClass RRCalledSeq;

IntArrayClass *AmbigSum;
    IntArrayClass *MutAmbigSum;
    IntArrayClass *RatioBin;
    IntArrayClass *MutRatioBin;
    IntArrayClass CalledCode;
    IntArrayClass MutCalledCode;

float *CalledSeqConf;
    float **Ratios;
    float *CalledRatio;
    float **Probabilities;

public:
    int GetCalledCode(int i)            {return CalledCode[i];};
    int GetMutCalledCode(int i)         {return MutCalledCode[i];};
    int GetMutRatioBin(int i, int j)    {return MutRatioBin[i][j];};
    int GetNumAmbiguities()             {return NumAmbiguities;};

float *GetRatios(int i)             {return Ratios[i];};
    float *GetProbabilities(int i)      {return Probabilities[i];};
    float  GetCalledSeqConf(int i)      {return CalledSeqConf[i];};
    float  GetCalledRatio(int i)        {return CalledRatio[i];};

char  GetWTSeq(int i)               {return WTSeq[i];};
    char *GetWTSeq()                    {return WTSeq();};
    char  GetMutWTSeq(int i)            {return MutWTSeq[i];};
    char *GetMutWTSeq()                 {return MutWTSeq();};
    char  GetCalledSeq(int i)           {return CalledSeq[i];};
    char *GetCalledSeq()                {return CalledSeq();};
    char  GetMutCalledSeq(int i)        {return MutCalledSeq[i];};
    char *GetMutCalledSeq()             {return MutCalledSeq();};
    char  GetRRCalledSeq(int i)         {return RRCalledSeq[i];};
    char *GetRRCalledSeq()              {return RRCalledSeq();};

IntArrayClass *GetAmbigSum()        {return AmbigSum;};
    IntArrayClass *GetRatioBin()        {return RatioBin;};
    IntArrayClass *GetCalledCode()      {return &CalledCode;};

void SetWTSeq(char *);
    void SetCalledSeq(char *);

int DetermineCalledCode(char);

void OutputWTSeq(int);
    void OutputWTSeq(int, char *);
    void OutputMutWTSeq(int, char *);
    void OutputCalledSeq(int);
    void OutputCalledSeq(int, char *);
    void OutputMutCalledSeq(int, char *);
    void OutputIntensityData(int, char *);
```

```
    void OutputSummaryData(int);
    void OutputIntensityData(int);
    void OutputAmbiguityData(int);
    void OutputAmbiguityCells(int);
    void OutputRatioData(int);
    void OutputCalledRatioData(int);
    void OutputProbabilityData(int);

void OutputRefAnalysisData(int, float **, CharArrayClass);

ResultsClass();
    ResultsClass(int, int, InputClass *);
    ~ResultsClass();
};
//////////////////////////////////////////////////////////////// endif
```

32

```
#include <string.h>
#include <stdlib.h>
#include <fstream.h>
#include <ctype.h>
#include <math.h>
#include <values.h>
#include <Sort.h>
#include <Bytes.h>
#include <StatFunctions.h>
#include <StatClass.h>
#include <StandardUnitClass.h>
#include <HeapSortIndex.h>
#include <ComplementSequence.h>
#include <IUPAC.h>

///////////////////////////////////////////////////////////
//
// NAME:             StandardUnitClass::ComputeProbabilities
//
// PURPOSE:          Computes the probabilities of ACGT being the
//                   correct call.
//
// PROCEDURES CALLED: PHI() - area of a normal distribution.
//                    var() - variance.
//
// INPUTS:           None
//
// OUTPUTS:          None
//
// GLOBAL OBJECTS:   None
//
// HISTORY:
//      NAME          DATE      DESCRIPTION
//      Chunwei Wang  4-12-95   Initial Code
//
///////////////////////////////////////////////////////////
void
StandardUnitClass::ComputeProbabilities()
{

// Local objects.

AtomClass *Atom;
    float *prob;
    float PHIxy, deno;
    float Pprime[MAXMISMATCHES], sum_Pprime;
    int i, j, k;

// Loop over the atoms of the unit.

for (i=0; i<this->NumAtoms; i++)
    {

// Get atom.

Atom = &this->AtomData[i];

// Get instance to store atom's probabilities.

prob = this->Probabilities[i];

// Compute the probability for each cell.
```

33

```
    sum_Pprime = 0;
    for(j = 0; j < MAXMISMATCHES; j++)
    {
        Pprime[j] = 1;
        for(k = 0; k < MAXMISMATCHES; k++)
        {
            if(Atom->GetStdv(j) == 0 &&
               Atom->GetStdv(k) == 0)
            {
                deno = 0.0001;
            }
            else
            {
                deno = sqrt(varIx_1y(Atom->GetStdv(j), Atom->GetStdv(k)));
            }

PHIxy = (j == k) ? 1.0
                : PHI((Atom->GetIntensity(j)-Atom->GetIntensity(k))/deno);

Pprime[j] *= PHIxy;
        }
        sum_Pprime += Pprime[j];
    } for(j = 0; j < MAXMISMATCHES; j++)
    {
        prob[j] = Pprime[j] / sum_Pprime;
    }
}
}
///////////////////////////////////////////////////////////////
///////////////////////////////////////////////////////////////
//
// NAME:            StandardUnitClass::ComputeProbUnknownSeq
//
// PURPOSE:         Computes called sequence based on probabilities
//                  and threshold
//
// PROCEDURES CALLED:
//
// INPUTS:          None
//
// OUTPUTS:         None
//
// GLOBAL OBJECTS:  None
//
// HISTORY:
//      NAME            DATE      DESCRIPTION
//      Derek Bernhart  6-17-94   Initial Code
//      Chunwei Wang    4-23-95   Added code for the Probability Method
//
///////////////////////////////////////////////////////////////
void
StandardUnitClass::ComputeProbUnknownSeq()
{

// Local objects.

AtomClass *Atom;
    float threshold;

float *prob, prob_sum, CalledConfidence;
    char CalledBase;
    CodeType CodeIndex;
```

34

```
    int CalledBase_num;

int i, j, k;
    int accd_index[MAXMISMATCHES];

// Get parameters.
    threshold = this->Input->Parameters.GetThreshold();

// Loop over the atoms of the unit.
    for (i=0; i<this->NumAtoms; i++)
    {

// Get atom.
        Atom = &this->AtomData[i];

// Get atom's probabilities.
        prob = this->Probabilities[i];

// Sort the prob array.
        HeapSortIndex(MAXMISMATCHES, prob, accd_index);

// Determine base.
        if (Atom->GetControlFlag(0))
        {
            if (abs(Atom->GetDesType(0)) == BLANK)
            {
                CodeIndex = BA;
                CalledBase = this->Input->BlankCol;
            }
            else
            {
                CodeIndex = CP;
                CalledBase = this->Input->CntrProbe;
            }
        }
        else
        {
            prob_sum = 0;
            CalledBase_num = 0;

for(j = MAXMISMATCHES-1; j >=0; j--)
            {
                prob_sum += prob[accd_index[j]];
                CalledBase_num |= (int) pow(2,accd_index[j]);
                if(prob_sum >= threshold)
                {
                    CalledBase = base2iupac[CalledBase_num];
                    CalledConfidence = prob_sum;

switch(toupper(CalledBase))
                    {
                      case 'A':
                        CodeIndex = A;
                        break;
                      case 'C':
```

35

```
          CodeIndex = C;
          break;
        case 'G':
          CodeIndex = G;
          break;
        case 'T':
          CodeIndex = T;
          break;
        case 'Y':
          CodeIndex = Y;
          break;
        case 'R':
          CodeIndex = R;
          break;
        case 'M':
          CodeIndex = M;
          break;
        case 'K':
          CodeIndex = K;
          break;
        case 'S':
          CodeIndex = S;
          break;
        case 'W':
          CodeIndex = W;
          break;
        case 'H':
          CodeIndex = H;
          break;
        case 'B':
          CodeIndex = B;
          break;
        case 'V':
          CodeIndex = V;
          break;
        case 'D':
          CodeIndex = D;
          break;
        case 'N':
          CodeIndex = N;
          break;
        case 'X':
          CodeIndex = X;
          break;
        default:
          break;
      }
      break;
    }
  }

// Increment code count and add to called code and sequence.

this->CalledCode.Add(CodeIndex);
    this->CalledSeq.Add(CalledBase);
    this->CalledSeqConf[i] = CalledConfidence;
  }
}
////////////////////////////////////////////////////////
```

```c
#include <math.h>
#define PI      3.141596
#define P       0.33267
#define ALPHA1  0.4361836
#define ALPHA2 -0.1201676
#define ALPHA3  0.9372980

////////////////////////////////////////////////////////////////
////////////////////////////////////////////////////////////////
//
// NAME:             varIx_Iy
//
// PURPOSE:          Calculate the variance of Ix-Iy.
//
// PROCEDURES CALLED: None
//
// INPUTS:           STDVx
//                   STDVy
//
// OUTPUTS:          var(Ix-Iy)
//
// GLOBAL OBJECTS:   None
//
// HISTORY:
//     NAME             DATE       DESCRIPTION
//     Chunwei Wang     4-95       Initial Code
//     Catherine Wilson 6-28-95    Integrated into Viewseq
//
////////////////////////////////////////////////////////////////
float varIx_Iy(float STDVx, float STDVy)
{
    return (STDVx * STDVx + STDVy * STDVy);
}

////////////////////////////////////////////////////////////////
////////////////////////////////////////////////////////////////
//
// NAME:             Z
//
// PURPOSE:          Calculate the Z value of x.
//
// PROCEDURES CALLED: None
//
// INPUTS:           x
//
// OUTPUTS:          Z(x)
//
// GLOBAL OBJECTS:   None
//
// HISTORY:
//     NAME             DATE       DESCRIPTION
//     Chunwei Wang     4-95       Initial Code
//     Catherine Wilson 6-28-95    Integrated into Viewseq
//
////////////////////////////////////////////////////////////////
float Z(float x)
{
    return (1/sqrt(2*PI) * exp(-x*x/2));
}

////////////////////////////////////////////////////////////////
////////////////////////////////////////////////////////////////
```

```
//
// NAME:      PHI
//
// PURPOSE:   Approximate the probability(area) in a normal distribution:
//            PHI(x) = integral( 1/sqrt(2*PI) * exp(-power(y,2)/2) * dy)
//                     (-inf,x)
//            if x >= 0;
//            PHI(x) = 1 - PHI(-x)   if x < 0
//
// PROCEDURES CALLED: None
//
// INPUTS:    X
//
// OUTPUTS:   PHI(X)
//
// GLOBAL OBJECTS: None
//
// HISTORY:
//    NAME              DATE       DESCRIPTION
//    Chunwei Wang      4-95       Initial Code
//    Catherine Wilson  6-28-95    Integrated into Viewseq
//
///////////////////////////////////////////////////////////////
float PHI(float X)
{
// approximation constants:
    float alpha[3] = {ALPHA1,ALPHA2,ALPHA3};

int i, num_items = 3;
    float t, t_power, x, sum, phi;

x = (X>=0) ? X : -X;

t = 1 / (1 + P * x);

sum = 0;
    t_power = 1;

for(i = 0; i < num_items; i++)
    {
        t_power *= t;
        sum += alpha[i] * t_power;
    } phi = 1 - Z(x) * sum;

return ((X>=0) ? phi : 1 - phi);
}
///////////////////////////////////////////////////////////////
```

38

```
#include <stdlib.h>
#include <fstream.h>
#include <malloc.h>
#include <string.h>
#include <ctype.h>
#include <values.h>
#include <Sort.h>
#include <HeapSortIndex.h>
#include <ResultsClass.h>
#include <AmbiguityClass.h>

/////////////////////////////////////////////////////////////
//
//  NAME:              ResultsClass::OutputProbabilityData
//
//  PURPOSE:           Output the probabilities of ACGT being correct call.
//                     Output file name: *.pb*.
//                     Output fields:
//                        Atom    - Atom number
//                        X       - X coordinate on the chip.
//                        Y       - Y coordinate on the chip.
//                        TProb   - Probability of 'T' being the correct call.
//                        GProb   - Probability of 'G' being the correct call.
//                        CProb   - Probability of 'C' being the correct call.
//                        AProb   - Probability of 'A' being the correct call.
//                        Sgl     - Called base if a single base is call.
//                        SglProb - Single base call probability.
//                        Dbl     - Called bases if two-base amb. is called.
//                        DblProb - Double base call probability.
//                        Trp     - Called bases if three-base amb. is called.
//                        TrpProb - Triple base call probability.
//
//  PROCEDURES CALLED: None
//
//  INPUTS:            UnitNumber      - Unit on chip.
//
//  OUTPUTS:           None
//
//  GLOBAL OBJECTS:    None
//
//  HISTORY:
//     NAME            DATE      DESCRIPTION
//     Chunwei Wang    4-10-95   Initial Code
//
/////////////////////////////////////////////////////////////
void
ResultsClass::OutputProbabilityData(int UnitNumber)
{

// Local objects.

AtomClass *Atom;

int i=0, j;
   float *prob;
   float prob_sum;
   int accd_index[MAXMISMATCHES];
   char CalledBase[MAXMISMATCHES];
   char *acgt = "acgt";

char Name[MAXFILELENGTH];

ofstream pbStream;
```

39

```
// Initialize char arrays.
    for (i=0; i<MAXFILELENGTH; i++)
        Name[i] = (char) 0;

// Get output filename and open file stream.
    sprintf(Name, "%spb%d", this->In->OutFilePrefix, UnitNumber);
    pbStream.open(Name, ios::out);
    if (!pbStream)
    {
        cout << "ERROR: can't open " << Name << endl;
        exit(1);
    }

// Print header.
    pbStream << "ATOM" << TAB;
    pbStream << "X" << TAB;
    pbStream << "Y" << TAB;
    pbStream << "AProb" << TAB;
    pbStream << "CProb" << TAB;
    pbStream << "GProb" << TAB;
    pbStream << "TProb" << TAB;
    pbStream << "Sgl" << TAB;
    pbStream << "SglProb" << TAB;
    pbStream << "Dbl" << TAB;
    pbStream << "DblProb" << TAB;
    pbStream << "Trp" << TAB;
    pbStream << "TrpProb" << endl;

// Print out desired data.
    pbStream.precision(2);
    for (i=0; i<this->RCNumAtoms; ++i)
    {
        Atom = &this->RCAtomData[i];

pbStream << i << TAB;
        pbStream << Atom->GetX(3) << TAB;
        pbStream << Atom->GetY(3) << TAB;

prob = this->GetProbabilities(i);

pbStream << prob[0] << TAB;
        pbStream << prob[1] << TAB;
        pbStream << prob[2] << TAB;
        pbStream << prob[3] << TAB;

HeapSortIndex(MAXMISMATCHES, prob, accd_index);

prob_sum = 0;

for(j = MAXMISMATCHES-1; j > 0; j--)
        {
            prob_sum += prob[accd_index[j]];
            CalledBase[MAXMISMATCHES-j-1] = acgt[accd_index[j]];
            CalledBase[MAXMISMATCHES-j] = '\0';

pbStream << CalledBase << TAB;
            pbStream << prob_sum << TAB;
        } pbStream << endl;
```

70

41

```
#ifndef ComputeConsensus_HEADER
define ComputeConsensus_HEADER include <SequenceClass.h>
include <AtomClass.h>
#include <LinkedList.h>

///////////////////////////////////////////////////////////
//
// NAME:          ComputeConsensus
//
///////////////////////////////////////////////////////////
float **ComputeConsensus(SequenceClass **Seqs, int , char *, int *,
                         AtomClass *, int, DoubleLinkedList *, int, float);

/////////////////////////////////////////////////////////// endif
```

42

```
#include <SequenceClass.h>
include <AtomClass.h>
#include <BlockUnitClass.h>
#include <OptimizeUnitClass.h>
#include <StandardUnitClass.h>
#include <Warning.h>
#include <MetaAtomDBClass.h>
#include <HeapSortIndex.h>
#include <LinkedList.h>
#include <stdio.h>
#include <string.h>
#include <Constants.h>
#include <IUPAC.h>
#include <math.h>
#include <values.h>

////////////////////////////////////////////////////////////
////////////////////////////////////////////////////////////
//
// NAME:               FindConsensusProbabilities
//
// PURPOSE:            Update consensus probabilities for another sequence.
//
// PROCEDURES CALLED:  None
//
// INPUTS:             Sequence, consensus method.
//
// OUTPUTS:            The product of probabilites array or the
//                     maximum probability array, depending on the method.
//
// GLOBAL OBJECTS:     None
//
// HISTORY:
//      NAME              DATE       DESCRIPTION
//      Chunwei Wang      2-7-95     Initial Code
//      Catherine Wilson  7-11-95    Integrated into Viewseq
//
////////////////////////////////////////////////////////////
void FindConsensusProbabilities(SequenceClass *Seq, float **Product, int Method)
{

// Local objects.

const float PROBZERO = 0.0000001;   // The product will be zero if any
                                        // probabilities are zero.

float *Probabilities;

int i,j;

AtomClass *Atom;
    UnitClass *Unit;

Unit = Seq->GetUnitData();

// Loop over atoms.

for(i=0; i<Seq->GetNumBases(); i++)
    {
        Atom = (*Unit)[i];

// Check if atom and chip data valid.
```

```
        if (Atom && Seq->GetChipData())
        {
            Probabilities = Seq->GetProbabilities(i);
// Determine the product of probabilities or maximum probability array.
            for(j=0; j<MAXMISMATCHES; j++)
            {
                if (Method == PRODUCT)
                {
// If one probability is 0, prevent Product = 0.
                    if (Probabilities[j] < MINFLOAT)
                        Product[i][j] *= PROBZERO;
                    else
                    {
                        if (Atom->GetDirection() == vFALSE)
                            Product[i][j] *= Probabilities[j];
// If reverse sequence, use complement of a,c,g or t.
                        else
                            Product[i][j] *= Probabilities[MAXMISMATCHES-1-j];
                    }
                }
                else if (Method == MAXIMUM)
                {
                    if (Atom->GetDirection() == vFALSE)
                    {
                        if (Product[i][j] < Probabilities[j])
                            Product[i][j] = Probabilities[j];
                    }
// If reverse sequence, use complement of a,c,g or t.
                    else
                    {
                        if (Product[i][j] < Probabilities[MAXMISMATCHES-1-j])
                            Product[i][j] = Probabilities[MAXMISMATCHES-1-j];
                    }
                }
            }
        }
    }
}
////////////////////////////////////////////////////////////////
////////////////////////////////////////////////////////////////
//
// NAME:              ComputeConsensus
//
// PURPOSE:           Find the Consensus Sequence from a group of Seqs,
//                    using one of two methods: Product, Maximum.
//
// PROCEDURES CALLED: FindConsensusProbabilities
//
// INPUTS:            A group of sequences, consensus method
//
// OUTPUTS:           Consensus sequence and their Atoms.
//
// GLOBAL OBJECTS:    None
//
```

44

```
// HISTORY:
//      NAME              DATE        DESCRIPTION
//      Chunwei Wang      2-7-95      Initial Code
//      Catherine Wilson  7-11-95     Integrated into Viewseq
//
////////////////////////////////////////////////////////////////
float **
ComputeConsensus
(
    SequenceClass    **Seqs,
    int              NumSeqs,
    char             *MetaBases,
    int              *MixFlag,
    AtomClass        *Atoms,
    int              NumBases,
    DoubleLinkedList *MetaDB,
    int              Method,
    float            Threshold
)
{

// Local objects.

int i, j, k;
    int acgtIndex[MAXMISMATCHES];
    int Dir;
    int CalledBase_num;

char *acgt="acgtACCT";
    char *File=NULL;
    char CalledBase;

float Sum;              // Sum used in normalizing.
    float **Product = NULL; // a,c,g,t consensus probabilites for each atom.
    float ProbSum;          // Called base confidence.
    //float MetaBasesConf[NumBases];

CellClass EmptyCell;
    AtomClass *Atom=NULL;
    ChipAtomDBClass *ChipAtomDB=NULL;
    ChipAtomDBClass *ChipEntry=NULL;
    ChipClass *ChipData=NULL;
    DoubleLinkedList *SeqMetaDB=NULL;

vbool FoundCalled;
    vbool ProbFlag = vTRUE;  // True if all sequences have probabilities UnitClass *Unit=Seqs[0]->GetUnitData();

// Check if all sequences have probabilities for(i=0; i<NumSeqs; i++)
    {
        if (Seqs[i]->GetProbabilities(0)==NULL)
            ProbFlag = vFALSE;
    } if (ProbFlag == vTRUE)
    {

// Allocate product memory.

Product = new float *[NumBases];

// Initialize product data.
```

45

```
        for(i=0; i<NumBases; i++)
        {
            Product[i] = new float[MAXMISMATCHES];

for(j=0; j<MAXMISMATCHES; j++)
            {
                if (Method == PRODUCT)
                    Product[i][j] = 1.0;
                else if (Method == MAXIMUM)
                    Product[i][j] = 0.0;
            }
        }

// Loop over sequences.

for(i=0; i<NumSeqs; i++)
        {

// Updates the consensus probabilities of a,c,g,t for each atom.

FindConsensusProbabilities(Seqs[i], Product, Method);

// Get meta database.

ChipData = Seqs[i]->GetChipData();
            SeqMetaDB = ChipData->GetChipMetaDB();

// Store meta database called from chip sequences.

if (SeqMetaDB->Entries() == 0)
            {
                ChipAtomDB = new ChipAtomDBClass;
                if (ChipData->In->XformType == XLQ)
                    File = ChipData->In->Parameters.GetUnkCellFile();
                else
                    File = ChipData->In->Parameters.GetUnkXformFile();
                ChipAtomDB->SetChipName(File);
                ChipAtomDB->SetUnit(Seqs[i]->GetUnitNumber());
                ChipAtomDB->SetID(i);
                ChipAtomDB->SetCommentOne(ChipData->In->CommentLineOne);
                ChipAtomDB->SetCommentTwo(ChipData->In->CommentLineTwo);
                ChipAtomDB->SetCommentAnalysis(ChipData->In->CommentAnalysis);
                MetaDB->Add(ChipAtomDB);
            }

// Store meta database called from meta sequences.

else
            {
                SeqMetaDB->InitIterator();
                while (ChipAtomDB = (ChipAtomDBClass *) ++(*SeqMetaDB))
                {

// Check if new database entry is unique.

if (MetaDB->Find(ChipAtomDB, CompareChipMetaAtomDB] == NULL)
                    {
                        ChipEntry = new ChipAtomDBClass;
                        ChipEntry->SetChipName(ChipAtomDB->GetChipName());
                        ChipEntry->SetUnit(ChipAtomDB->GetUnit());
                        ChipEntry->SetID(ChipAtomDB->GetID());
                        ChipEntry->SetCommentOne(ChipAtomDB->GetCommentOne());
```

76

```
                    ChipEntry->SetCommentTwo(ChipAtomDB->GetCommentTwo());
                    ChipEntry->SetCommentAnalysis(ChipAtomDB->GetCommentAnalysis());
                    MetaDB->Add(ChipEntry);
                }
            }
        }
    }

// Normalize Results.

for (k=0; k<NumBases; k++)
    {
        Sum = 0;
        for (j=0; j<MAXMISMATCHES; j++)
        {
            Sum += Product[k][j];
        }

// Check if 0 or 4 and if (Sum == 0 || Sum == 4)
            MetaBases[k] = ' ';

else
            MetaBases[k] = '.';

for (j=0; j<MAXMISMATCHES; j++)
        {
            if (Sum > 0)
                Product[k][j] /= Sum;
        }
    }

// Loop over atoms.

for(i=0; i<NumBases; i++)
    {

// Process those bases which have data if (MetaBases[i] == '.')
        {

HeapSortIndex(MAXMISMATCHES, Product[i], acgtIndex);

// Initialize locals.

ProbSum = 0;
            FoundCalled = vFALSE;
            CalledBase_num = 0;

// Determine called base.

for (j=MAXMISMATCHES-1; j>0; j--)
            {
                ProbSum += Product[i][acgtIndex[j]];

CalledBase_num |= (int) pow(2,acgtIndex[j]);

if (FoundCalled == vFALSE && ProbSum >= Threshold)
                {
                    CalledBase = base2iupac[CalledBase_num];
```

```
                    FoundCalled = vTRUE;
                }
            } if (FoundCalled == vFALSE)
            {
                ProbSum += Product[i][acgtIndex[j]];
                CalledBase_num |= (int) pow(2,acgtIndex[j]);
                CalledBase = base2iupac[CalledBase_num];
            }

MetaBases[i] = CalledBase;
            //MetaBasesConf[i] = ProbSum;
        }
// Get sequence data.

//Dir = Seqs[0]->GetComplementFlag();
            //if (Dir)
                //*MixFlag = vTRUE;

// Copy empty atom to output parameter Atoms[j].

for(k = 0; k < MAXMISMATCHES; k++)
                Atoms->SetEntry(k, EmptyCell);

Atoms->SetWTIndex(0);
            Atoms->SetBackGround(0);
            Atoms->SetDirection(0);
            Atoms->SetEditBase(0);
            Atoms->SetChipIndex(0);
            Atoms->SetStatData(NULL);
            Atoms->SetAtomPos(0, i);

// Increment atom.

++Atoms;
        }

MetaBases[i] = '\0';

// If only one sequence reset mix strain flag.

//if (NumSeqs == 1)
            *MixFlag = vFALSE;

// Return the new probability array return Product;
    }
    else
        return NULL;

}
/////////////////////////////////////////////////////////////////
```

What is claimed is:

1. In a computer system, a method of calling an unknown base in a sample nucleic acid sequence, the method comprising the steps of:

inputting a plurality of hybridization probe intensities, each of the probe intensities indicating hybridization affinity between a sample nucleic acid sequence comprising an unknown base and a nucleic acid probe;

for each probe intensity of the plurality of probe intensities, determining a probability that the nucleic acid probe for the probe intensity best hybridizes with the sample nucleic acid sequence; and calling the unknown base according to the nucleic acid probe with the highest probability.

2. The method of claim 1, wherein the highest probability indicates a confidence that the unknown base is called correctly.

3. The method of claim 1, wherein each nucleic acid probe has a different base at an interrogation position.

4. The method of claim 3, wherein each probability indicates the likelihood that the unknown base is complementary to a base at the interrogation position in the nucleic acid probe.

5. The method of claim 1, wherein each probe intensity of the plurality of probe intensities is calculated from a plurality of intensity values.

6. The method of claim 5, wherein each probe intensity of the plurality of probe intensities is a mean of the plurality of intensity values.

7. The method of claim 5, further comprising the step of calculating a standard deviation for each intensity value of the plurality of intensity values of a probe intensity.

8. The method of claim 1, further comprising the step of comparing the highest probability to a probability threshold.

9. The method of claim 8, wherein the unknown base is called according to the nucleic acid probe with the highest probability if the highest probability exceeds the probability threshold.

10. The method of claim 8, further comprising the steps of:

producing a sum of the highest probability and a next highest probability;

comparing the sum to the probability threshold; and calling the unknown base according to the nucleic acid probes with the highest and next highest probabilities if the sum exceeds the probability threshold.

11. The method of claim 10, wherein the sum indicates a confidence that the unknown base is called correctly if the sum exceeds the probability threshold.

12. The method of claim 1, wherein each probability is determined by a first equation:

$$Prob(X) = Prob(I_x > max(I_y))_{Y \neq X}$$

where X and Y include A, C, G, or T(U); I is a probe intensity associated with a subscripted base; and max represents a maximum of the probe intensities.

13. The method of claim 12, wherein the first equation is solved by a second equation:

$$prob(I_x > max(I_y)) \approx \Pi prob(I_x > I_y)_{Y \neq X}$$

where X and Y include A, C, G, or T(U) and Π represents a product of probabilities that $I_x$ is greater than other of the probabilities.

14. The method of claim 13, wherein the second equation is solved by a third equation:

$$\text{Prob}(I_X > I_Y) = \Phi\left(\frac{I_X - I_Y}{\sqrt{\sigma_X^2 - \sigma_Y^2}}\right)_{Y \neq X}$$

where X and Y include A, C, G, or T(U) and a represents a standard deviation of ($\sigma^2$ being a variance) of intensities for a subscripted base.

15. The method of claim 14, wherein the third equation is solved by a fourth equation:

$$\Phi(X) = \int_{-\infty}^{X} \frac{1}{\sqrt{2\pi}} e^{-\frac{y^2}{2}} dy$$

where Φ represents a density equation of standard normal distribution.

16. The method of claim 1, wherein the unknown base is called as being A, C, G, or T(U).

17. A computer program that calls an unknown base in a sample nucleic acid sequence, comprising:

code that receives as input a plurality of hybridization probe intensities, each of the probe intensities indicating hybridization affinity between a sample nucleic acid sequence comprising an unknown base and a nucleic acid probe;

code that determines for each probe intensity of the plurality of probe intensities a probability that the corresponding nucleic acid probe best hybridizes with the sample nucleic acid sequence; and code that calls the unknown base according to the nucleic acid probe with the highest associated probability;

wherein the codes are stored on a tangible medium.

18. The computer program of claim 17, wherein the highest probability indicates a confidence that the unknown base is called correctly.

19. The computer program of claim 17, wherein each nucleic acid probe has a different base at an interrogation position.

20. The computer program of claim 19, wherein each probability indicates the likelihood that the unknown base is complementary to a base at the interrogation position in the nucleic acid probe.

21. The computer program of claim 17, wherein each probe intensity of the plurality of probe intensities is calculated from a plurality of intensity values.

22. The computer program of claim 21, wherein each probe intensity of the plurality of probe intensities is a mean of the plurality of intensity values.

23. The computer program of claim 21, further comprising the step of calculating a standard deviation for each intensity value of the plurality of intensity values of a probe intensity.

24. The computer program of claim 17, further comprising the step of comparing the highest probability to a probability threshold.

25. The computer program of claim 24, wherein the unknown base is called according to the nucleic acid probe with the highest probability if the highest probability exceeds the probability threshold.

26. The computer program of claim 24, further comprising the steps of:

producing a sum of the highest probability and a next highest probability;

comparing the sum to the probability threshold; and calling the unknown base according to the nucleic acid probes with the highest and next highest probabilities if the sum exceeds the probability threshold.

27. The computer program of claim 26, wherein the sum indicates a confidence that the unknown base is called correctly if the sum exceeds the probability threshold.

28. A system that calls an unknown base in a sample nucleic acid sequence, comprising:

a processor; and a computer readable medium coupled to the processor, said computer readable medium storing a computer program comprising:

code that receives as input a plurality of hybridization probe intensities, each of the probe intensities indicating hybridization affinity between a sample nucleic acid sequence comprising an unknown base and a nucleic acid probe;

code that determines for each probe intensity of the plurality of probe intensities a probability that the corresponding nucleic acid probe best hybridizes with the sample nucleic acid sequence; and code that calls the unknown base according to the nucleic acid probe with the highest associated probability.

29. The computer program of claim 28, wherein the highest probability indicates a confidence that the unknown base is called correctly.

30. The computer program of claim 28, wherein each nucleic acid probe has a different base at an interrogation position.

31. The computer program of claim 30, wherein each probability indicates the likelihood that the unknown base is complementary to a base at the interrogation position in the nucleic acid probe.

32. The computer program of claim 28, wherein each probe intensity of the plurality of probe intensities is calculated from a plurality of intensity values.

33. The computer program of claim 32, wherein each probe intensity of the plurality of probe intensities is a mean of the plurality of intensity values.

34. The computer program of claim 32, further comprising the step of calculating a standard deviation for each intensity value of the plurality of intensity values of a probe intensity.

35. The computer program of claim 28, further comprising the step of comparing the highest probability to a probability threshold.

36. The computer program of claim 35, wherein the unknown base is called according to the nucleic acid probe with the highest probability if the highest probability exceeds the probability threshold.

37. The computer program of claim 35, further comprising the steps of:

producing a sum of the highest probability and a next highest probability;

comparing the sum to the probability threshold; and calling the unknown base according to the nucleic acid probes with the highest and next highest probabilities if the sum exceeds the probability threshold.

38. The computer program of claim 37, wherein the sum indicates a confidence that the unknown base is called correctly if the sum exceeds the probability threshold.

* * * * *